`US010914732B2`

(12) United States Patent
Giehring

(10) Patent No.: US 10,914,732 B2
(45) Date of Patent: Feb. 9, 2021

(54) METHOD AND DEVICE FOR DETERMINING BIOLOGICAL ANALYTES

(71) Applicant: PAIA BIOTECH GMBH, Cologne (DE)

(72) Inventor: Sebastian Giehring, Cologne (DE)

(73) Assignee: PAIA BIOTECH GMBH, Cologne (DE)

( * ) Notice: Subject to any disclaimer, the term of this patent is extended or adjusted under 35 U.S.C. 154(b) by 742 days.

(21) Appl. No.: 15/124,076

(22) PCT Filed: Mar. 5, 2015

(86) PCT No.: PCT/EP2015/054671
§ 371 (c)(1),
(2) Date: Sep. 7, 2016

(87) PCT Pub. No.: WO2015/135840
PCT Pub. Date: Sep. 17, 2015

(65) Prior Publication Data
US 2017/0016890 A1    Jan. 19, 2017

(30) Foreign Application Priority Data

Mar. 10, 2014  (EP) .................................. 14158692

(51) Int. Cl.
*G01N 33/553* (2006.01)
*G01N 33/543* (2006.01)
(Continued)

(52) U.S. Cl.
CPC ...... *G01N 33/54326* (2013.01); *B01L 3/5025* (2013.01); *B01L 3/5085* (2013.01);
(Continued)

(58) Field of Classification Search
CPC .......... B01L 3/50; B01L 3/502; B01L 3/5085; B01L 8011/22; B01L 22/0668;
(Continued)

(56) References Cited

U.S. PATENT DOCUMENTS 5,457,527 A * 10/1995 Manns .................. B01L 3/5085
356/246
5,674,699 A    10/1997 Saunders et al.
(Continued)

FOREIGN PATENT DOCUMENTS

EP         0371265 A1    6/1990
JP       2006162466 A    6/2006
(Continued)

OTHER PUBLICATIONS

International Search Report dated Aug. 5, 2015, issued in counterpart Application No. PCT/EP2015/054671.

*Primary Examiner* — Christopher L Chin
(74) *Attorney, Agent, or Firm* — McBee Moore & Vanik IP, LLC

(57) ABSTRACT

The invention relates to a method for quantitatively determining biological analytes in an aqueous solution in the presence of one or more functionalised surfaces, wherein the aqueous solution comprises at least one type of biological analyte and at least one type of fluorescence marker, characterised in that the quantity and/or concentration of the biological analyte or analytes is determined by measuring the fluorescence emission of the unbound fluorescence markers, as well as to a devices for carrying out said method.

9 Claims, 11 Drawing Sheets

(51) Int. Cl.
*B01L 3/00* (2006.01)
*G01N 21/64* (2006.01)
*G01N 33/533* (2006.01)
*G01N 21/03* (2006.01)

(52) U.S. Cl.
CPC ....... *G01N 21/6428* (2013.01); *G01N 33/533* (2013.01); *G01N 33/54366* (2013.01); *B01L 2200/0647* (2013.01); *B01L 2200/0668* (2013.01); *B01L 2300/0654* (2013.01); *B01L 2300/0829* (2013.01); *B01L 2300/0848* (2013.01); *B01L 2300/0851* (2013.01); *B01L 2300/0858* (2013.01); *B01L 2300/0887* (2013.01); *B01L 2300/168* (2013.01); *B01L 2400/043* (2013.01); *B01L 2400/0409* (2013.01); *B01L 2400/0457* (2013.01); *G01N 21/0303* (2013.01); *G01N 21/6452* (2013.01); *G01N 2021/6439* (2013.01); *G01N 2021/6482* (2013.01); *G01N 2201/0642* (2013.01)

(58) Field of Classification Search
CPC ..... B01L 2300/0654; B01L 2300/0829; B01L 2300/0848; B01L 2300/0851; B01L 2300/0858; B01L 2300/0887; B01L 2300/168; B01L 2400/0409; B01L 2400/0457; G01N 33/54313; G01N 33/536; G01N 33/537; G01N 33/538; G01N 33/54366; G01N 21/6428; G01N 21/0303; G01N 21/0325; G01N 2021/0382

USPC ....... 356/246; 422/407; 435/288.4; 436/536, 436/538, 541, 809
See application file for complete search history.

(56) References Cited

U.S. PATENT DOCUMENTS

| | | | | |
|---|---|---|---|---|
| 5,792,426 | A | * | 8/1998 | Portmann ............ B01L 3/5085 206/443 |
| 6,051,191 | A | * | 4/2000 | Ireland ................. B01L 3/5085 356/246 |
| 2005/0214167 | A1 | | 9/2005 | Archibald et al. |
| 2007/0154356 | A1 | | 7/2007 | Modavid et al. |
| 2009/0251683 | A1 | | 10/2009 | Wardlaw et al. |
| 2010/0028935 | A1 | | 2/2010 | Ciaiolo et al. |
| 2010/0103410 | A1 | * | 4/2010 | Silbergleit ........... B01L 3/5085 356/246 |
| 2014/0017709 | A1 | * | 1/2014 | Lowe .................... C12Q 1/001 435/7.92 |

FOREIGN PATENT DOCUMENTS

| | | |
|---|---|---|
| JP | 2007155549 A | 6/2007 |
| WO | 0052451 A1 | 9/2000 |
| WO | 02073198 A2 | 9/2002 |

\* cited by examiner

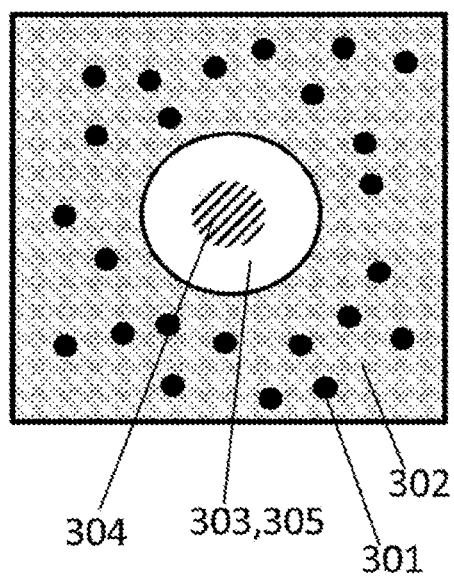
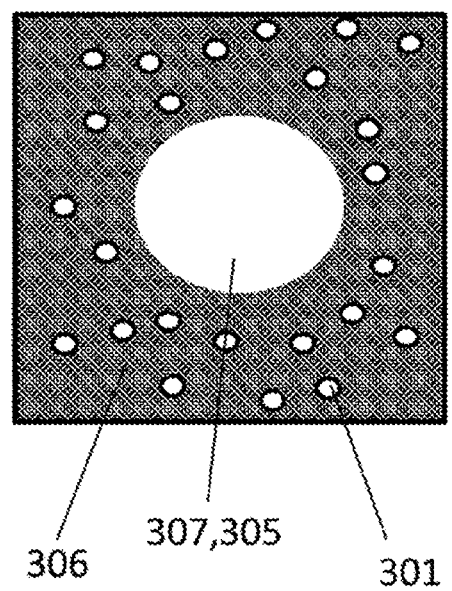
Fig. 3a
Fig. 3b
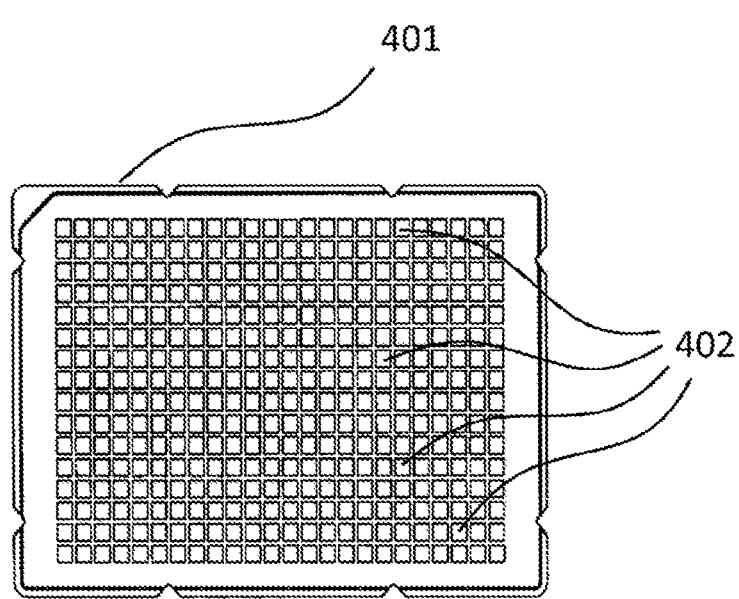
Fig. 4

METHOD AND DEVICE FOR DETERMINING BIOLOGICAL ANALYTES

CROSS REFERENCE TO RELATED APPLICATIONS

This application is a § 371 National Stage Application of PCT/EP2015/054671, filed Mar. 5, 2015, which claims priority to EP 14158692.5, filed Mar. 10, 2014.

BACKGROUND

Field of the Invention

The application relates to a method for qualitatively and/or quantitatively determining biological analytes by measuring the luminescence of the unbound luminescence markers, as well as to a device therefore and to the use of the device.

Description of Related Art

The quantitative and/or qualitative determination and the counting of biological units such as, for example, nucleic acids, proteins, antibodies, bacteria, viruses or cells, what are known as biological analytes, is an important method in the development of modern active ingredients, in other research in the field of the life sciences and in the production of biopharmaceuticals.

The demands made of a method or process for determining biological analytes are generally high and vary greatly, in particular as regards concentration ranges, accuracy of measurement and sample preparation. Even when determining the same biological analytes, the measuring methods can vary greatly depending on the purpose of the measurement. In diagnostics, for example, a protein is measured in a very low concentration in blood serum samples, while in biotechnological production methods proteins are situated in a culture medium, where they are present in concentrations which are several powers of ten higher. Furthermore, the methods can be such that, as well as determining the analytes, they are also able to provide further information, for example about the activity or the affinity and the specificity. The enzyme-linked immunosorbent assay, abbreviated as "ELISA assay" or "ELISA method", has for decades been established as the standard method for determining particular biological analytes, in particular proteins and antibodies. It is an immunoassay to which an enzymatic colour reaction is coupled. The principle of the ELISA assay consists substantially in binding the biological analyte (for example a protein) to a surface (for example a microplate) by catcher molecules. The catcher molecules are typically antibodies, fragments thereof or also protein A or protein G.

In the widely used sandwich ELISA method, an antibody is used as the catcher and then a detection antibody is bound to the analyte at a second binding site. An enzyme (for example horseradish peroxidase, HRP) is coupled to the detection antibody, which enzyme, by addition of a substrate for the enzyme, initiates an enzymatic reaction, by means of which dyes form. Typical substrates are tetramethylbenzidine (TMB) or diaminobenzidine (DAB), which colour the solution blue or brown. Before the colouring can be measured by spectrometry, the enzymatic reaction must be stopped by adding a stop reagent. The amount of dye produced by the HRP is proportional to the amount of analyte and is then measured with a suitable detection device, generally a UV/VIS photometer. Also known in this context are enzyme substrates which yield a fluorescent product (for example resorufin), which is detected with a fluorescence meter. By means of the enzymatic reaction, a large number of dye molecules can be produced in the sandwich ELISA assay for each bound analyte molecule. As a result of this enhancement effect, the sandwich ELISA assay is generally very sensitive.

Also common are ELISA methods which are characterised in that the enzyme-conjugated detection antibody is bound not directly to the analyte but to a further primary antibody which in turn binds specifically to the analyte. This variant is employed if enzyme-conjugated primary antibodies are not available and is overall more sensitive for non-specific binding of the antibodies with one another.

The direct ELISA methods are distinguished in that there is used as the catcher molecule not an antibody but an antigen, which is bound by the antibody to be measured. Detection takes place analogously to the methods described above via detection antibodies.

A disadvantage of the ELISA method is that it involves a large number of incubation steps and washing steps, which often have to be carried out repeatedly. These working steps are not or are only partially automatable and are therefore predominantly carried out manually at present. This makes the ELISA assay intensive in terms of personnel and time. In the ELISA method, test times of from 4 to 5 hours are often required, so that the ELISA assay cannot be used in processes in which a quick result is required or a large number of samples are to be measured, for example in HTS (high throughput screening).

A further disadvantage of the ELISA method is that the large number of working steps gives rise to a relatively large total error, since each of the working steps causes its own variance and those variances add up to the total variance.

Attempts have already been made to make the ELISA method quicker and less intensive in terms of personnel and cost. One modification of the ELISA method is the "fluorescent immunoassay" (FIA). Fluorescent immunoassays are generally simpler to carry out than the above-mentioned "conventional" ELISA method.

By using a detection antibody labelled with a fluorescent dye, it is possible in the fluorescent immunoassay to work without an enzymatic reaction. The number of method steps is thereby reduced, and deviations based on fluctuating enzyme activity are thereby eliminated. Fluorescent immunoassays can be carried out in homogeneous or heterogeneous systems. In heterogeneous systems, special particles are often used and the fluorescence at the particles is measured, while in homogeneous fluorescent immunoassays the fluorescence is measured in solution. Several steps of the conventional ELISA method are thus saved, and the test time is reduced to usually from 2 to 3 hours. However, dispensing with the enzyme reaction often has the result that the sensitivity in these methods is lower than in the ELISA.

An example of a homogeneous fluorescent immunoassay is the Delfia technology (dissociation-enhanced lanthanide fluorescent immunoassay) from Perkin-Elmer. In the method, europium complexes bound to the detection antibody are brought into solution and then measured with fluorescence, in particular time-resolved fluorescence. A further known method is the TR-FRET technology, which is offered by Cisbio as HTRF technology (homogeneous time resolved fluorescence), and the LANCE technology (lanthanide chelate excite) from Perkin-Elmer.

The above-mentioned TR-FRET method is based on the principle that two antibodies binding one another are so labelled with fluorescent dyes that the dyes are able to carry out a fluorescence resonance transfer (FRET) when they are brought into spatial proximity, that is to say when they are bound to one another. A FRET donor is bound to one antibody and a FRET accepter is bound to the other antibody. FRET only works when the distance between the antibodies is less than 10 nm. If the above-mentioned antibodies bind to one another, the FRET donor can be excited to fluorescence with light of a specific wavelength. By means of the emitted light of the FRET donor, the FRET accepter is excited to fluorescence emission, and this is measured. That is to say, the fluorescence emission of the FRET accepter can only be measured if the two antibodies (in the solution) are bound to one another. If such a solution is placed in a vessel and an analyte which binds to the FRET accepter or the FRET donor is added thereto, one of the two FRET partners is displaced from the complex, so that the fluorescence emission of the FRET accepter diminishes in dependence on the concentration of the analyte.

FRET is a technique which is widely used in research to detect the binding of two molecules. However, it is also known that the efficiency of the transfer is greatly dependent on the composition of the sample. In order to make a routine method out of this technique, special FRET donors consisting of a complex between a europium or terbium ion and a macrocycle (for example based on tris-bipyridines) are used in TR-FRET technology. These donors have the property of emitting longer-lasting fluorescence in comparison to other fluorescent substances which may be present in the sample. The fluorescence measurement therefore takes place only in a defined time interval after a flash of light. As a result, a period of time is allowed to elapse until the interfering fluorescence from the sample has subsided and only the FRET fluorescence still occurs. Nevertheless, both the emission of the FRET donor and that of the FRET accepter must be measured in TR-FRET technology, and the ratio thereof must be determined so that matrix influences and quenching of the fluorescence emission can be compensated for mathematically. In order for this compensation to function optimally, the two emission wavelengths must be measured simultaneously and not sequentially. This means that the measuring devices for accurate TR-FRET measurements must be equipped with two detectors. Typical measuring ranges for the TR-FRET method are approximately from 10 to 5000 ng/ml of antibody.

A further modification of the conventional ELISA assay is the AlphaLISA method from Perkin-Elmer. Here, a pair of antibodies labelled with probes is brought into spatial proximity by binding to different binding sites of the same analyte.

In contrast to TR-FRET, the probes used are not fluorophores having a low molecular weight but donor and accepter particles (donor and accepter beads) having a size of approximately from 250 to 350 nm. By irradiating the donor beads with laser light having a wavelength of 680 nm, singlet oxygen is released therefrom and triggers light emission having a wavelength of approximately 615 nm at the accepter bead situated in proximity. The light emission is then measured and serves to quantify the analyte. Unlike in TR-FRET, the molecules carrying probes cannot be added simultaneously in the AlphaLISA, so that a second reaction time (incubation time) is necessary and the protocol is consequently lengthened.

The donor beads are light-sensitive. It is possible to work with them only in the dark or in green light, which represents a considerable disadvantage of the method. The laser to be used in the AlphaLISA assay is often only incorporated into special fluorescence plate readers, which makes the test expensive since it is necessary to have or purchase the devices.

In particle-supported heterogeneous fluorescent immunoassays, as in the conventional ELISA methods, the biological analyte is first bound to the surface, in this case to functionalised insoluble particles, by catcher molecules. After a washing step, fluorescence-labelled detection antibodies are added, the whole is mixed, and then the unbound fluorescence-labelled detection antibodies are removed. The quantity of fluorescence-labelled detection antibodies bound to the particles is measured, the content of the biological analyte being determined via the fluorescence of the fluorescence markers bound to the particles. Such a method, or determination, is known (see overview article by C. F. Woolley and M. A. Hayes, "Recent developments in emerging microimmunoassays", Bioanalysis (2013) 5(2)).

In the "GYROS technology" used by Gyros AB, microfluidic structures are used to centrifuge small sample quantities onto particle beds (usually in the form of small columns), on which there form fluorescence-labelled sandwich complexes, which are measured. The entire microfluidic system is produced in round plastics discs, the liquids (for example dissolved catcher molecules, sample, washing solutions) being forced outwards through the channels by the rotation of the disc (as in the case of a CD-ROM) about its central axis. Since GYROS technology can only be used to measure concentrations of greater than or equal to 1 ng/ml, it is used above all in biotechnological process development and control.

Quanterix offers a technology by the name of SIMOA (single molecule array), in which sandwich immunocomplexes are formed on particles. The particles are then distributed microfluidically on a chip to hundreds of thousands of cavities (wells/indentations), each of which is able to receive only one particle. For the detection, the cavities are then closed and an enzyme is activated, which produces a fluorescent dye. At very low concentrations of analyte, there is on average less than one analyte molecule in a cavity, that is to say there are only cavities with or without fluorescence, which are then counted. This assay is therefore also referred to as "digital ELISA". Detection limits below $10^{-15}$ M can be achieved therewith (see Rissin et al.: "Single-molecule enzyme-linked immuosorbent assays detects serum proteins at subfemtomolar concentrations", Nature Biotechnology, 28(6), 595).

GYROS and SIMOA are multi-stage processes, and complex microstructured consumables (such as, for example, the discs mentioned above) as well as dedicated and expensive readers are required.

For measuring fluorescence-labelled immunocomplexes which are bound to particles, it is also possible to use flow cytometers. Here, the particles are transported individually through a flow system to a measuring point at which they are excited to fluorescence by laser light. Measurement with a flow cytometer has the advantage that different analytes can be determined at the same time. The particles used for that purpose carry a colour coding on the inside, that is to say are doped with differentiable fluorescent dyes, each of the colours representing binding to a specific analyte. For the measurement, two lasers are used simultaneously. The first laser identifies the particle type via the colour coding, and the second laser identifies the content of bound immunocomplex. In XMAP technology (Luminex Corp.), up to one hundred different analytes can be detected in one test procedure; this is referred to as multiplex applications.

In addition to the above-mentioned methods, further measuring methods are used, in particular in the field of process development and control for producing recombinant proteins and antibodies, which are less complex than ELISA, for example biolayer interferometry (BLI, from Pall ForteBio) or surface plasmon resonance (SPR, GE Healthcare, Biacore). These methods, in particular BLI, permit a higher degree of automation and are based on the binding of the analyte to surfaces which are typically coated with protein A or G or with antibodies.

Binding the analytes to the surface brings about a change in the optical property of the surface, which change is measured. The quantity of molecules bound to the surface is calculated therefrom. Thus, measuring ranges of from 0.5 to 2000 µg/ml are achieved with BLI and measuring ranges of from 0.15 to 10 µg/ml are achieved with SPR. A disadvantage of this method is that comparatively expensive and specialised measuring devices are required, as are special consumables (for example sensors and chips).

All the methods mentioned above are disadvantageous as regards their complex test procedure. They often require many working steps for the quantification of biological analytes and are therefore complex to perform. Likewise, there are applications and scientific problems in which it is desirable to have available a simplified method, based on an immunoassay, with which more highly concentrated samples can be measured and/or with which results are obtained quickly. It is further desirable to have available an immunoassay with which special antibodies can be determined in diverse liquids, such as, for example, serum or cell culture supernatants. This is an advantage in particular in the case of the recombinant (technical) production of antibodies in order to be able to make qualitative and/or quantitative statements simply, quickly and inexpensively during the production of proteins. It is further desirable to have available a method, in particular an immunoassay, for determining biological analytes which requires only a small number of working steps, whereby time and reagents can be saved. There is therefore a need for a simple and rapid method for determining biological analytes, preferably in the form of an immunoassay, which is simple to carry out and avoids all or at least some of the disadvantages mentioned above.

SUMMARY

Accordingly, the object of the present invention is to provide a method with which all or at least some of the above-mentioned disadvantages are avoided.

The object has been achieved by the method described in the claims, in particular by the device according to the invention and the use thereof. The important factor is that the luminescence or fluorescence emission of the unbound luminescence or fluorescence markers is measured, so that biological analytes can be determined simply, quickly and inexpensively.

Accordingly, the invention relates to a method for determining (especially for quantifying) biological analytes in an aqueous solution in the presence of one or more functionalised surfaces, wherein the aqueous solution comprises at least one type of biological analyte and at least one type of luminescence marker, preferably fluorescence marker, characterised in that the quantity and/or concentration of the biological analyte or analytes is determined by measuring the luminescence emission, preferably fluorescence emission, of the unbound luminescence markers, preferably fluorescence markers.

BRIEF DESCRIPTION OF THE DRAWINGS

FIGS. 1-7 depict embodiments as described herein.

DETAILED DESCRIPTION OF A PREFERRED EMBODIMENT

Figure 1A:
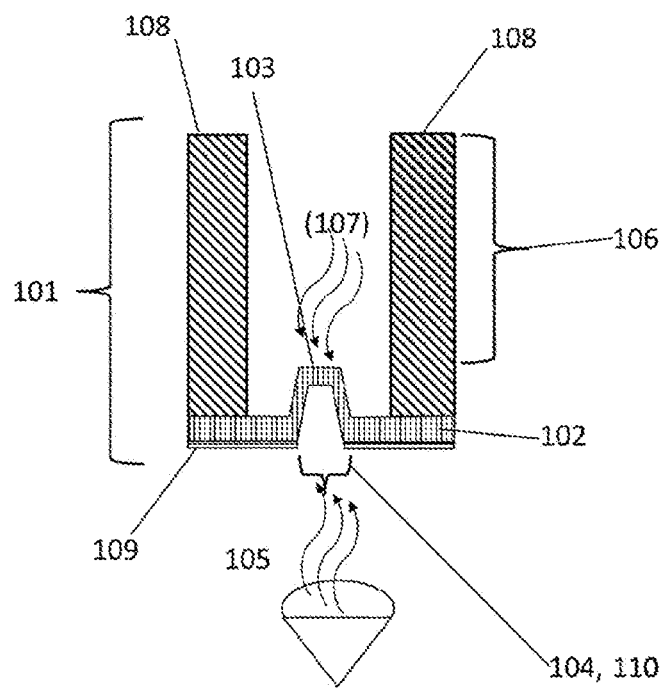

Any desired assays can be carried out with the method according to the invention. The method according to the invention is preferably an immunoassay, in particular an immunoassay selected from a group consisting of direct immunoassay, sandwich immunoassay, displacement immunoassay (also called inhibition assay herein), competitive immunoassay and secondary immunoassay.

In one embodiment [V-1], there are used as the functionalised surfaces in the method according to the invention functionalised particles of polymer or a polymer mixture, on the surface of which particles there are catcher molecules which bind to the biological analyte or analytes and/or to the fluorescence marker or markers. The functionalised particles advantageously have a mean diameter in the range of from approximately 20 to approximately 200 µm or in the range of from approximately 80 to approximately 200 µm.

In one embodiment [V-2], functionalised magnetic particles are used as the functionalised surfaces in the method according to the invention. The magnetic particles advantageously have a mean diameter in the range of from approximately 1 to approximately 100 µm. Magnetic particles have ferromagnetic or superparamagnetic properties. They conventionally comprise a magnetic core of ferrite or magnetite, which is surrounded by a shell of polymers or polymer mixtures. They are functionalised according to the non-magnetic particles, that is to say equipped with catcher molecules.

In one embodiment [V-3], the method according to the invention comprises the following steps:

(a) introducing at least one type of functionalised particles or functionalised magnetic particles into a measuring chamber which has a detection region, which is accessible to light through the bottom of the measuring chamber, and a separation region which is not accessible to light;

(b) introducing a sample comprising at least one type of biological analyte into the measuring chamber;

(c) introducing at least one type of fluorescence marker into the measuring chamber;

(c') mixing the introduced particles, sample and fluorescence markers in the measuring chamber;

(c") separating the unbound fluorescence markers from bound fluorescence markers (preferably by sedimentation or centrifugation), so that the bound fluorescence markers are in the separation region;

(d) measuring the fluorescence emission of the unbound fluorescence markers in the detection region; and (e) determining the quantity and/or concentration of the biological analyte or analytes.

Measuring chamber is here also understood as being a microplate well that is equipped according to the invention. The method according to the invention is preferably carried out with microplates whose wells are equipped as measuring chambers according to the invention.

Steps (a), (b) and (c) can be carried out before or after a further method step, wherein the further method step comprises introducing further test components or substances, such as, for example, primary antibodies or auxiliary substances, such as detergents, into the measuring chamber.

Steps (a), (b) and (c) can take place sequentially, or at least two of the steps take place simultaneously.

In a variant [V-4] of the method according to the invention, step (a) and/or step (c) is carried out before the remaining method steps, preferably with a large time interval relative to the remaining steps.

In a variant [V-5] of the method according to the invention, the functionalised particles are magnetic (magnetisable).

In a further variant [V-6], functionalised magnetic particles are used and step (c″) is carried out by sedimentation and by applying a temporary or permanent magnetic field.

In one embodiment [V-7] of the method according to the invention, a fluorescence microscope is used for measuring the fluorescence emission of the unbound fluorescence markers in step (d). In the devices, measuring chambers or microplates according to the invention which are to be used, the opaque layer on the bottom can then be omitted. The fluorescence microscope must be so adjusted that it measures only the fluorescence emission that occurs in the detection region, while the fluorescence emission coming from the separation region is masked out.

Microplates are known. They contain a plurality of cavities (also called wells, cups, indentations or recesses) which are isolated from one another. The number of cavities on a microplate can vary. The following arrangements are available commercially:

2×3 (6 wells), 4×3 (12 wells), 4×6 (24 wells), 6×8 (48 wells), 8×12 (96 wells), 16×24 (384 wells), 32×48 (1536 wells). The bottoms of the cups of the commercially available microplates can have different shapes. The following bottoms are available commercially: F-bottom (flat bottom), C-bottom (flat bottom with minimally rounded corners), V-bottom (conically tapering bottom) and U-bottom (U-shaped well). Microplates having an F-, C- or U-bottom, into which the device is introduced, are particularly suitable according to the invention.

Particle-supported methods for determining biological analytes are known (see U.S. Pat. No. 4,731,337B, DE 102004038163A, WO 86/04684, WO 94/29722, U.S. Pat. No. 4,115,535B, WO 2011/045022). These methods are all based on measuring the fluorescence of bound fluorescence markers.

Devices for separating insoluble constituents from aqueous solutions are known. WO 2011/031236 and US 2010/0028935, for example, describe specially shaped devices for separating corpuscular particles from an aqueous solution in order thus to increase the accuracy of measurement in transmission spectroscopy and absorption spectroscopy. However, these devices are not suitable for use in the method according to the invention since it is not possible with those devices reliably to measure the luminescence of unbound luminescence markers, or the fluorescence of unbound fluorescence markers, in order to quantify the biological analyte or analytes to be determined.

The method therefore also provides special devices with which the method according to the invention can be carried out.

Accordingly, the invention relates also to a device [0] for determining biological analytes by measuring the luminescence of the unbound luminescence markers, in which bound and unbound luminescence markers in an aqueous solution are spatially and optically separated from one another using one or more functionalised surfaces, wherein the device has for the separation an at least partly transparent structural element, wherein the base of the device, apart from the base area of the structural element, is opaque and the aqueous solution comprises at least one type of biological analyte and at least one type of luminescence marker, and wherein at least one type of biological analyte and optionally at least one type of luminescence marker binds to one or more functionalised surfaces.

The invention relates further to a measuring chamber for use in the method according to the invention, in which functionalised magnetic particles are used. The bound luminescence markers, preferably fluorescence markers, are separated from the unbound luminescence markers by directed sedimentation with the aid of an opaque magnetic element placed beneath the measuring chamber. The magnetic element has apertures which are so arranged that measuring windows are formed on the bottom (base) of the measuring chamber. The magnetic element can be permanently connected to the base, or it is removable. The measuring chamber does not have a structural element.

By means of the magnetic field, the sedimentation of the functionalised magnetic particles is so guided that no particles settle above the measuring window. The luminescence, preferably fluorescence, is measured with a fluorescence meter through the measuring window in the bottom of the measuring chamber.

The invention relates further to the use of the above-mentioned measuring chamber, or of a microplate that is equipped with at least one such measuring chamber, in the method according to the invention, wherein functional magnetic particles are likewise used.

In one embodiment [A] of the device [0] according to the invention, one or more functionalised surfaces in the form of functionalised particles are introduced into the device according to the invention, wherein the bound luminescence markers are situated in the separation region of the device and the unbound luminescence markers are situated in the detection region, wherein they are preferably homogeneously distributed therein.

In one embodiment [B] of the device [0] according to the invention, there are one or more functionalised surfaces inside the device, preferably in the region of the device that is situated beneath the end of the structural element remote from the base, preferably that is situated on the base of the device. Separation takes place by binding of the biological analyte and the luminescence marker to one or more of the optionally immobilised functionalised surfaces situated in the device.

In a further embodiment [C], the invention relates to a device, as described above or in embodiment [A] or [B], in which the structural element is in the form of a protrusion (preferably in the form of an upwardly tapering protrusion), the cross section of which can have any desired geometry (for example circular, rectangular, triangular), wherein the end of the structural element that is remote from the base of the device is such that no test components, in particular no particles, settle there. It can be flat, for example, or have a convex shape and/or have a small diameter.

The structural element situated in a measuring chamber can have the shape of a mandrel, cone, truncated cone, pyramid or truncated pyramid, the base area of which is n-cornered, where n represents an integer in the range of from 3 to 10, preferably 3, 4, 5, 6, 7 or 8. It can further have a shape which is derived from a cone or a pyramid, for example a round-based cone or a 4-sided square-based pyramid.

The structural element can further have an optical component, for example a lens, at the end that is remote from the base of the device.

The structural element is transparent. It is made of a suitable transparent material or material mixture. It is important that the material does not have any autofluorescence which interferes with the measurement. Transparent materials are known and can easily be selected by a person skilled in the art. Such materials are, for example, polystyrene, COC (cycloolefin copolymer), polypropylene or polymethyl methacrylate (PMMA). Polypropylene and PMMA are very suitable. Polystyrene, in particular when it is processed while hot, has a certain degree of autofluorescence (Young et al., *Anal Chem.* 2013 Jan. 2; 85(1): 44-49) and is therefore not preferred according to the invention.

The material or material mixture can be used in a thickness (layer thickness) of ≤1 mm. Preferred thicknesses are in the following ranges: from approximately 0.05 to approximately 0.5 mm, from approximately 0.1 to approximately 0.45 mm, from approximately 0.15 to approximately 0.4 mm, from approximately 0.2 to approximately 0.4 mm, or from approximately 0.2 to approximately 0.35 mm.

In a further embodiment [D], the invention relates to a device, as described above or in one of embodiments [A], [B] or [C], in which there is a separation region and a measurement region (detection region), wherein the measurement region has a transparent measuring window or is optically connected to such a measuring window.

In a further embodiment [E], the invention relates to a device, as described above or in one of embodiments [A], [B], [C] or [D], in which the base of the structural element is in the form of a measuring window. The luminescence is then measured by means of a luminescence meter, preferably a fluorescence meter. The excitation and the detection of the emission take place from beneath the device.

When the base and the end of the structural element that is situated in a device or measuring chamber are optically connected to one another, excitation light irradiated in from the base of the device passes through the structural element into the detection region, where it excites the unbound luminescence markers, preferably fluorescence markers, to emission, which is then measured likewise from the base of the device. The end of the structural element and the base then together form the measuring window. When selecting a suitable shape for the structural element, it must be ensured that particles do not interfere with the excitation and emission light. It is therefore particularly advantageous if the end of the structural element has a convex shape and the structural element is in the form of a protrusion which tapers upwards. If the end is flat, it is advantageous if the surface is small and/or the surface is such that no particles or only a non-interfering number of particles (also referred to in the present case as "substantially no") are able to settle. In the case of flat ends too, it is advantageous if the protrusion tapers towards the end that is remote from the base.

In a further embodiment [F], the invention relates to a microplate in each of the recesses, cups or wells of which there is integrated a device as described above or in one of embodiments [0], [A], [B], [C], [D] or [E].

Accordingly, the invention relates in one embodiment [F-1] to a microplate for carrying out the method according to the invention, characterised in that there is introduced into at least one well of the microplate a device which has an at least partly transparent structural element which is in the form of an upwardly tapering protrusion and the cross section of which can have any desired geometry, wherein the end of the structural element that is remote from the base is such that substantially no test components settle there, and wherein the base of the device, apart from the base area of the structural element, is opaque, and wherein the edges of the well form the side edges of a measuring chamber.

In a further embodiment [F-2], the invention relates to the microplate as described in embodiment [F-1], characterised in that the original bottom of the microplate is replaced by a one-piece base having structural elements, wherein a structural element is situated in each of the wells of the microplate, and wherein the base, apart from the base area of the structural elements, is coated with an opaque layer.

In this case, the base is made of the same material as the structural elements and the criteria mentioned in connection with the structural elements as regards material properties and layer thickness apply for the selection of the material from which the base is formed.

The invention relates also to the production of the microplate described as embodiment [F-2], comprising the following steps:

(x) replacing the bottom of a microplate by a base having structural elements, which base preferably has as many structural elements as there are wells in the microplate;

(y) connecting the base to the microplate; and (z) applying an opaque layer to the underside of the base, wherein the base area of the structural element is kept free.

The connection of the base to the microplate and the application of an opaque layer take place as described below in the same context.

The one-piece base having structural elements can be produced by shaping methods, for example by injection moulding methods, additive production methods (for example 3D printing) or thermoforming (hot forming, deep drawing or vacuum forming).

It is of course possible that a structural element is not present in each of the wells of a microplate. Likewise, it is possible that differently shaped structural elements are present in the wells of the microplate. A one-piece base having structural elements can thus have structural elements of different shapes.

In a further embodiment [G], the invention relates to a measuring chamber containing a device as described above or in one of embodiments [0], [A], [B], [C], [D] or [E].

In a further embodiment [H], the invention relates to the use of the device, measuring chamber or microplate, as described above or in one of embodiments [0], [A], [B], [C], [D], [E], [F] or [G], in an immunoassay, in particular direct immunoassay, sandwich immunoassay, competitive immunoassay or secondary immunoassay, wherein the luminescence markers are then preferably fluorescence markers, for qualitatively or quantitatively determining biological analytes by measuring the luminescence of the unbound luminescence markers.

In addition to methods described above, the invention relates further to a method for qualitatively and/or quantitatively determining biological analytes using the device, measuring chamber or microplate according to the invention, in particular as described above or in one of embodiments [0], [A], [B], [C], [D], [E], [F] or [G], which method comprises the following steps:

(a) introducing at least one type of functionalised surface into the device;

(b) introducing a sample comprising at least one type of biological analyte into the device;

(c) introducing at least one type of luminescence marker into the device;

(d) measuring the luminescence emission of the unbound luminescence markers; and (e) determining the quantity and/or concentration of the biological analytes.

According to the invention, functionalised surfaces can already be present in the device, or they are introduced into the device alone or together with the measuring solution (sample) in the method according to the invention.

In one embodiment of the invention, functionalised particles are used as the functionalised surfaces.

In the method according to the invention, several types of functionalised surfaces/particles can be present, or several types of functionalisation can be present on a surface/particle surface. That is to say, the nature of the functionalisation of the surface can be different. This has the result that several types of biological analytes can be measured by the method according to the invention and in the device and measuring chamber according to the invention or with the microplate according to the invention. To that end, a distinct luminescence marker which is to be excited and/or emits with a different wavelength must be used for each of the analytes.

If functionalised magnetic particles are used, the above applies correspondingly.

In connection with the present invention, the term "functionalised" means that catcher molecules (also called "catchers" hereinbelow) are present on a surface, preferably on a particle surface. For the functionalisation of surfaces or particle surfaces, the surface is populated with at least one type of catcher molecule. Catcher molecules are molecules which bind physically or chemically to the biological analyte or analytes and/or to the luminescence marker or markers. It is irrelevant whether the particles are magnetic or non-magnetic. Both types of particles can be functionalised as described herein.

According to the invention, "functionalise" also means loading magnetic or non-magnetic particles with suitable metal ions, as described hereinbelow in connection with immobilised metal affinity chromatography (IMAC), so that the metal ion complexes formed (for example $NTA-Ni^{2+}$) form the catcher molecules, which then bind test components that have the corresponding tags.

For competitive assays, it is necessary for the functionalised surfaces, in particular particle surfaces, to have catchers to which both the biological analyte and the luminescence marker can bind physically and/or chemically at the same binding site. For the remaining assays, the catchers are to be such that that they bind only the biological analyte or analytes or, if desired, the luminescence marker or markers, preferably fluorescence markers.

The same applies if functionalised magnetic particles are used.

In a functionalisation variant, the catcher molecule has only binding sites that are selected specifically for one type of biological analyte, while in another variant the catcher molecule has a plurality of different binding sites, each binding site being so selected that it binds only a special biological analyte. With this variant, it is possible that different types of biological analytes bind to the functionalised surface.

If different types of biological analytes are to be measured at the same time, it is also possible in the method according to the invention to use differently functionalised (magnetic) particles in a measuring chamber.

One functionalisation variant comprises equipping the surfaces with different types of catcher molecules, each of the catcher molecules having at least one binding site for the biological analyte to be determined.

If functionalised particles or functionalised magnetic particles which are capable of binding several types of biological analytes are used in the method according to the invention, a distinct luminescence marker, preferably fluorescence marker, which is to be excited and/or emits with a different wavelength must be used for each of the analytes.

If the method according to the invention is to be carried out reliably, in particular when it is a direct (immuno)assay, sandwich (immuno)assay or secondary (immuno)assay, it is important that neither the catcher molecules nor the surfaces or particle surfaces bind specifically or non-specifically to test components other than the biological analyte or analytes. Exceptions are the competitive (immuno)assay and the displacement assay. In the competitive (immuno)assay, the catcher can bind the luminescence marker and the specific biological analyte at the same binding site. In the displacement assay, the catcher binds the luminescence marker, preferably the fluorescence marker.

Catchers suitable for functionalising surfaces and particle surfaces are known and are so selected that the desired test component or the desired test components bind to the catcher. Suitable catchers are mostly proteins (for example antibodies) which are optionally bound to the surfaces or particle surfaces by linker systems. The surface or particle surface can be populated with catchers by covalent or non-covalent binding. If one of the test components (for example the biological analyte) is an antibody, then the catcher is usually a protein. Known catchers for antibodies are, for example, protein A from *Staphylococcus aureus* and protein G from streptococci.

The same applies if functionalised magnetic particles are used.

Examples of surfaces equipped with a linker system are streptavidin-coated particles as are described in greater detail hereinbelow, for example Streptavidin Mag-Sepharose® particles (VWR, Art. No. 28-9857-38). A further example is agarose particles which carry nitriloacetic acid (NTA) or iminoacetic acid groups (IDA) on their surface, which particles form very stable complexes with metal ions and are suitable for binding to the His-tag labelled protein.

A common material consisting of porous material that is suitable for producing functionalised particles is agarose, which is available commercially under the name Sepharose™ (GE Healthcare). Sepharose, or agarose, is obtainable in different degrees of crosslinking and with different binding capacities. Prior to functionalisation, that is to say loading with catchers, the agarose particles are activated with a chemical in order to ensure efficient binding to catcher molecules. A suitable chemical for the activation is CNBr.

As already described, common catcher molecules are proteins. In order to bind proteins to surfaces, in particular particle surfaces, it is possible to use chemicals which function as linkers between the surface and the catcher molecule (for example streptavidin or homologues thereof (for example avidin, neutravidin)). Streptavidin or its homologues and biotin enter into a stable bond, so that any biotinylated protein binds to (particle) surfaces treated with streptavidin. The same applies if functionalised magnetic particles are used.

The biotinylation of proteins is known and is a standard method in biochemistry. There is usually used for the biotinylation an active ester (for example NHS, N-hydroxysuccinimide) with which biotin is coupled to free amino functions of a catcher protein. Biotinylated catcher proteins are usually bound to (magnetic) particles treated with streptavidin or homologues thereof.

Catcher proteins which comprise protein affinity tags can be bound to a (particle) surface via metal complexes. To that end, use is substantially made of the principle that certain amino acids form stable complexes with suitable metal ions (for example $Co^{2+}$, $Ni^{2+}$, $Cu^{2+}$ and $Zn^{2+}$). Such amino acids can be present naturally in the protein or they can be introduced into the protein as polypeptides, as what are known as "tags". Common tags are Arg-tag, c-Myc-tag, FLAG-tag and His-tag. The metal ions are bound to the (particle) surface with the aid of NTA (nitriloacetic acid), CMA (carboxymethyl aspartate) or IDA (iminoacetic acid). In the above-mentioned functionalisation, the same principles as are otherwise applied in the chromatographic purification of proteins, in particular in immobilised metal affinity chromatography (IMAC), are substantially used.

By using the above-mentioned principles, a person skilled in the art can readily adapt the method according to the invention to his particular needs in that the functionalised (magnetic) particles can individually be adapted to the assay to be used or to the biological analyte or analytes to be determined.

In the case where the functionalised surfaces are already present in the device, the invention relates in one embodiment to the fact that the introduction of the functionalised surfaces into the device, that is to say step (a), is carried out as a step (a'), namely treating at least one surface inside the device, preferably the base of the device, wherein the end of the structural element that is remote from the base is not treated, with a coating buffer that promotes binding of the catchers to the base, and adding at least one type of catcher, wherein the catchers are preferably added in solution.

Accordingly, the invention relates also to a device, to a measuring chamber according to the invention and to a microplate according to the invention in which at least one surface of the device, preferably the base of the device, is functionalised, wherein the end of the structural element that is remote from the base is not functionalised. Treated surfaces of a device are here also referred to as "stationary" surfaces.

After addition of the catchers, it is advantageous if the coating buffer acts at the desired site provided for functionalisation for several hours or overnight. Coating buffers suitable for populating surfaces with catcher molecules are known. An example thereof is a basic carbonate buffer with which, for example, the catcher molecule protein A can be bound at a desired site, for example on the base of the device.

The functionalisation of the base of the device, of the measuring chamber according to the invention and of the microplate according to the invention can take place by streptavidin, so that a plurality of different catchers, which have previously each been provided (conjugated) with biotin groups, are bound at the desired site.

By selecting suitable functionalised surfaces, it is possible to influence the test duration. In principle, a large functionalised surface increases the probability that the biological analyte or analytes to be measured, and if desired and provided the luminescence marker or markers, will come into contact with catchers on account of diffusion. By selecting a suitable size for the surface and the type and number of the catchers present thereon, the speed of the measurement can be influenced. In order to accelerate the method according to the invention, it is preferred to use large surfaces on which a plurality of catchers are situated. This applies to particle surfaces as well as to stationary surfaces.

A further factor which influences the speed of the method according to the invention, in addition to the size of the functionalised surface used, is the binding capacity thereof. In the case of functionalised particles, their binding capacity is understood as being: capacity to bind a specific quantity of biological analyte to the functionalised particle in relation to the amount or weight, mass of functionalised particles present. A further speed-determining parameter in the method according to the invention is, as described in greater detail below, the careful mixing of the test components. It is thereby immaterial whether the particles are magnetic or non-magnetic.

The functionalised (magnetic) particles to be used as functionalised surfaces in the method according to the invention are available commercially or are correspondingly prepared individually for the method.

For the preparation of such individually functionalised particles there can be used in particular particles of synthetic or natural polymers, for example polystyrene, latex, agarose, polylactide or PMMA, as well as polysaccharides. Particles of porous materials, such as, for example, agarose, are preferred. Particularly suitable are commercially available particles which are used for the chromatographic purification of biological analytes, for example proteins. They are conventionally supplied in the form of a slurry. The above applies analogously to magnetic particles, wherein the synthetic or natural polymers surround the magnetic core.

The non-magnetic particles which can be used according to the invention are often spherical particles and have typical mean diameters in the range of from approximately 0.1 to approximately 200 µm. Preferred particles according to the invention have mean diameters in the range of from approximately 20 to approximately 200 µm, in particular from approximately 80 to approximately 200 µm, and do not bind non-specifically to the test components. Particles which have a binding capacity of more than 200 mg IgG or analyte per ml are preferred according to the invention.

The magnetic particles (also called "magnetic beads") which can be used according to the invention are those which are usually used for isolating or analysing biological analytes (see, for example, WO 2006/112771). The polymer coating of magnetic particles usually consists of sugars, polyvinyl alcohol or of silicates. The magnetic particles can be functionalised in a manner analogous to that described for the particles or they are available commercially in the form of functionalised magnetic particles (for example Protein A Mag-Sepharose® particles from GE Healthcare Art. No. 28-9440-06). Particularly suitable magnetic particles according to the invention have a coating of porous material, for example agarose, and have a core of ferrite or magnetite (for example Mag-Sepharose® particles).

Magnetic particles are likewise spherical particles and have typical mean diameters in the range of from approximately 1 to approximately 100 µm.

The functionalised magnetic or non-magnetic particles to be used in combination with a specific biological analyte can easily be determined by a person skilled in the art, and in some cases such combinations are already in use in the further developed immunoassay methods of the prior art.

The following also applies when functionalised magnetic particles are used.

In the method according to the invention, steps (a) (optionally (a')), (b) and (c) can be carried out one after another, that is to say sequentially, or at least two of steps (a), (b) and (c) take place simultaneously, for example by placing functionalised surfaces in the device, followed by the measuring solution, which contains the sample and the luminescence markers. Alternatively, the sample containing the analyte is placed in the device, and the luminescence marker and the functionalised surface in the form of functionalised particles are added thereto. In the case of sequential addition, the sequence of the steps is not usually important. It is possible to carry out step (b) before step (a) and (c), or step (b) before step (c) and (a), or step (c) before step (a) or (b). In competitive immunoassays, it is advantageous if step (b) and step (c) are carried out simultaneously. If a device that already has functionalised surfaces is used, step (a) is omitted.

In the method according to the invention, step (a) and step (c) are preferably carried out, simultaneously or sequentially, before the remaining method steps. Likewise preferably, step (a) or step (c) is carried out before the remaining method steps.

The time interval between steps (a) and/or (c) and the remaining method steps can be small or large (for example several hours, days, weeks, months or years). If the interval is greater than 12 hours, it is advantageous if the test components introduced in steps (a) and/or (c), that is to say the functionalised (magnetic) particles and/or fluorescence markers that are introduced, are present in dried form in the measuring chamber. The measuring chambers are dried at room temperature, preferably at an elevated temperature of not more than 37° C., preferably 35° C. The duration of the drying is generally governed by the quantity of aqueous solution introduced into the measuring chamber. Conventional drying times are in the range of from 12 to 24 hours.

Before drying, further substances can optionally be introduced into the measuring chamber, which further substances are to ensure that the functionality/activity of the (magnetic) particles and/or of the luminescence markers or fluorescence markers is retained after drying. Suitable substances are BSA, sugars or detergents such as Tween 20.

Accordingly, the invention relates also to the measuring chambers and microplates according to the invention in which there are present, in each case in the dried state, (i) at least one type of functionalised particle or functionalised magnetic particle and at least one type of fluorescence marker, or (ii) at least one type of functionalised particle or functionalised magnetic particle, or (iii) at least one type of fluorescence marker, and to the use thereof in the method according to the invention.

The invention relates likewise to the production thereof. To that end, the procedure is as described above, namely by drying or freeze drying the corresponding test component after it has been introduced into the measuring chamber according to the invention.

If measuring chambers are used in which at least one type of functionalised particle or functionalised magnetic particle and/or at least one type of fluorescence marker, in the dried state, is already present, the step or steps with which the test component in question is added are omitted in the method according to the invention. For example, if the functionalised (magnetic) particles are already dried, the introduction of functionalised (magnetic) particles, that is to say step (a), is omitted.

In the method according to the invention, bonds form between the test components, which bonds are dependent on the affinities of the test components for one another and the concentrations thereof. It is necessary for the method according to the invention that the quantity of unbound luminescence markers under given and constant test conditions is dependent only on the quantity of biological analyte.

Figure 6A:
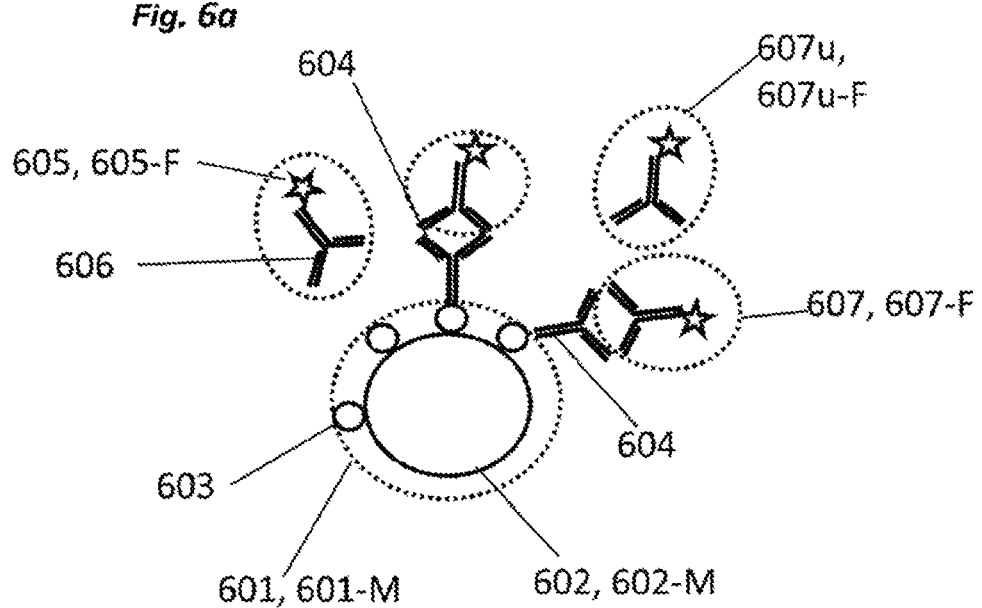
Figure 6B:
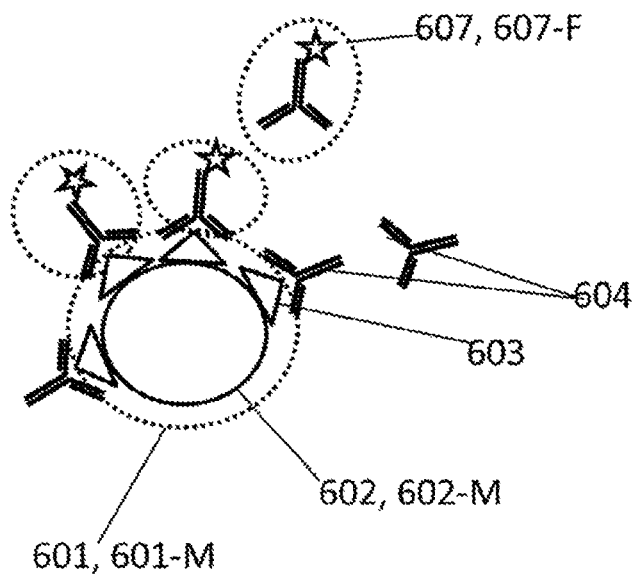
Figure 6C:
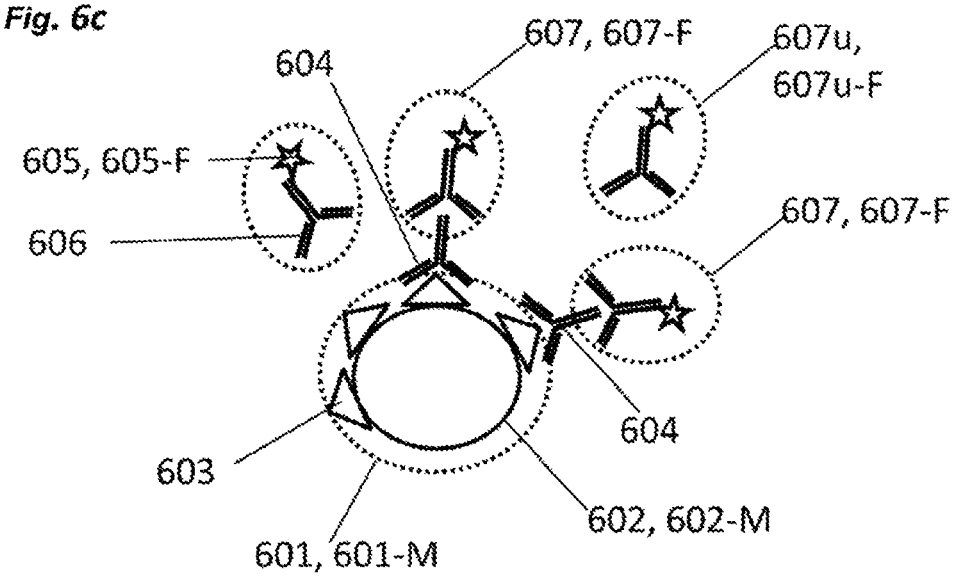
Figure 7A:
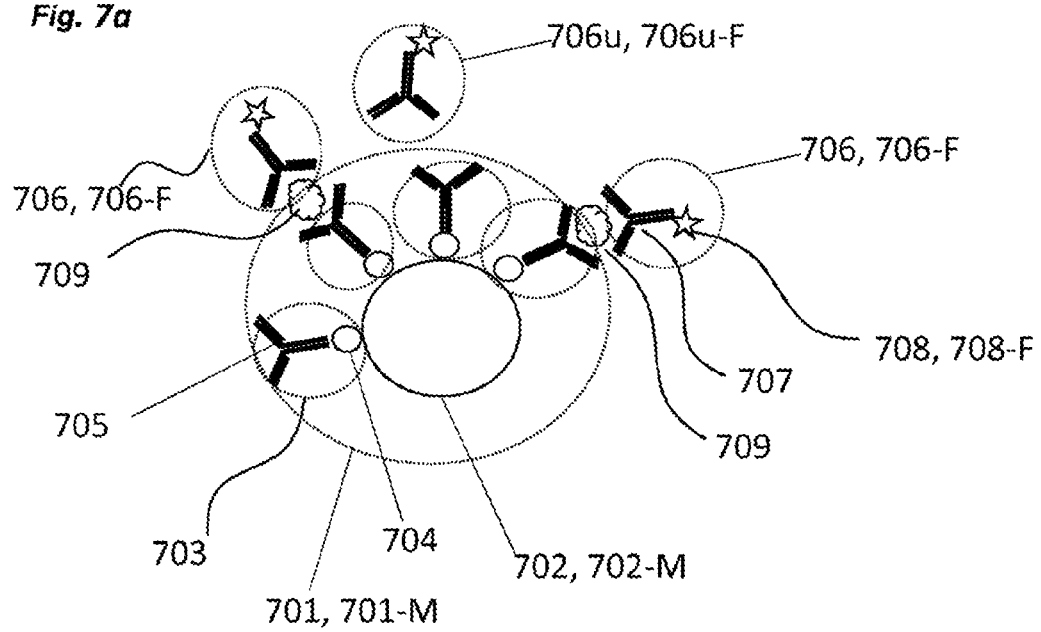

In one embodiment of the invention, the luminescence marker and the catcher each bind to the biological analyte at different sites (epitopes) (shown schematically in FIGS. 6a, 6c and 7a).

In a further embodiment of the invention, the luminescence marker and the biological analyte can each bind to the catcher molecule at the same site (shown schematically in FIG. 6b).

Figure 7B:
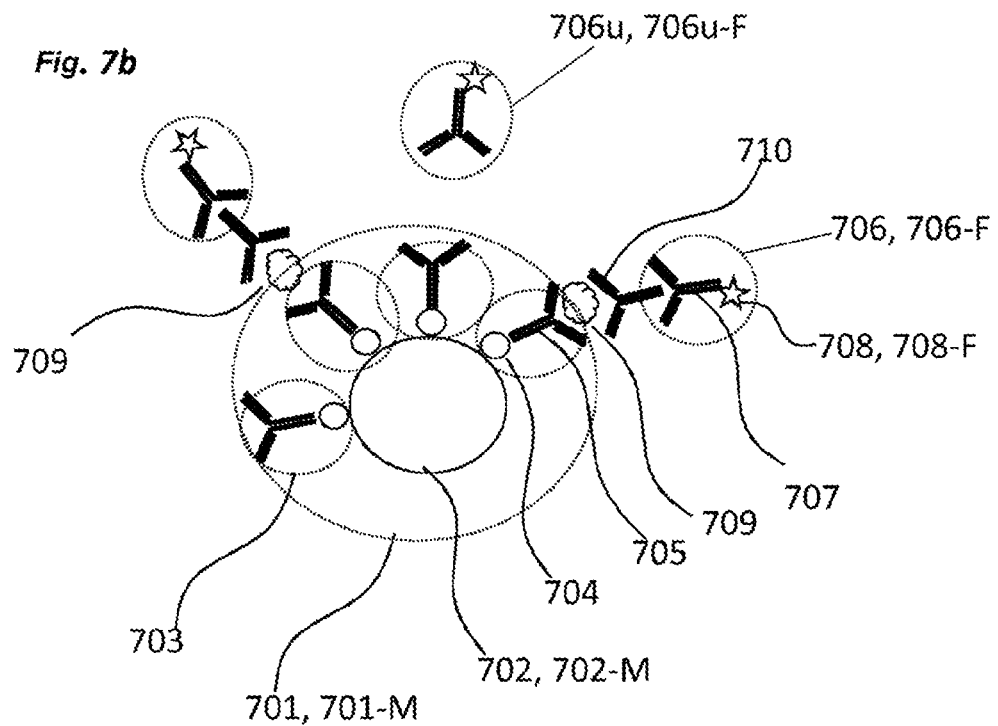

In a further embodiment of the invention, a primary antibody binds to the biological analyte instead of the luminescence marker, and the luminescence marker binds to the primary antibody (shown schematically in FIG. 7b).

In order to accelerate the formation of a bond, it is expedient to mix the test components thoroughly once all the test components have been introduced into the device, measuring chamber or microplate according to the invention. Mixing can take place manually or in an automated manner. The quicker the test components come into contact, the quicker the equilibrium is established and thus the biological analyte is measured/determined. The same applies if functionalised magnetic particles are used.

If it is desired to carry out the method more quickly, it is possible to dispense with establishing equilibrium. In this case, it is important to observe the same incubation times and conditions for all samples and calibrators.

For automated mixing, the unit in which the device according to the invention is situated (for example measuring chamber or microplate) is placed onto shakers (shaking devices) which are conventional in the laboratory. Such shaking devices are known. The optimum shaking speed can be found by simple methods. The use of a vortex apparatus is also conceivable.

The aim of mixing is to increase the probability of the test components coming into contact with one another, so that the desired bonds form as rapidly as possible and equilibration of the binding of the components is achieved quickly. The time required for equilibration of the binding of the components can vary and can easily be found. With optimal mixing, times in the range of from 15 to 30 minutes are usually required to achieve equilibration of the binding of the components that is sufficient for the measurement.

Alternatively to free diffusion or shaking, the probability of the test components coming into contact with one another, in particular of the biological analyte coming into contact with a catcher molecule, can be increased if the functionalised surfaces (preferably in the form of functionalised particles) are introduced into fluidic systems or microfluidic systems. In such systems, the biological analyte or analytes to be determined actively wash over the surfaces, so that the biological analyte or analytes accumulate on the functionalised surface (preferably functionalised particles). Microfluidic systems are often used to increase the sensitivity of detection in difficult samples, for example human serum.

Luminescence markers according to the invention can bind the desired test components (in particular the biological analyte or analytes) and at the same time are capable of emitting light. All conceivable luminescence markers can be used in the device according to the invention and in the method according to the invention. Fluorescence markers are preferably used.

Within the scope of the present invention, the expression "bound luminescence marker" is understood as meaning all luminescence markers which are bound to the functionalised surfaces directly or via further test components (for example via analyte or a primary antibody). At the same time, the term "unbound" luminescence or fluorescence marker refers to those markers which are not bound to the functionalised surface either directly or via further test components.

Luminescence or fluorescence markers which bind to specific biological analytes and/or functionalised surfaces are known and are available commercially. There are suitable, for example, Alexa 647- or Alexa 488-conjugated antibody fragments (for example Alexa 647-conjugated AffiniPure F(ab')$_2$ fragment goat anti-human IgG F(ab')$_2$ specific and polyclonal rabbit anti-hen IgY (H+L)-Alexa Fluor 488, Alexa 488 AffiniPure F(ab')$_2$ fragment goat anti-human IgG, F(ab')$_2$ specific) or fluorescein isothiocyanate (FITC)-conjugated polyclonal chicken anti-human IgG (H+L) antibody and R-phycoerythrin AffiniPure F(ab')$_2$ fragment goat anti-human IgG, Fcγ fragment specific.

Luminescence or fluorescence markers can also be produced individually. To that end, a luminescent or fluorescent dye is linked to a biological molecule (for example protein, antibody, antibody fragment) which has a suitable binding site and is able to bind the desired test component (preferably the biological analyte or analytes to be determined). Linking takes place by common methods, for example by using luminescent or fluorescent dyes which are equipped with NHS ester or maleimide groups and can thus be coupled to antibodies and proteins. The linking can additionally be streptavidin-mediated, in a manner similar to that described above, by binding a biotinylated protein to a luminescent or fluorescent dye equipped with streptavidin. The natural fluorescent proteins, such as, for example, GFP (green fluorescent protein) and its derivatives, can be used as fluorescence markers either alone or together with other proteins, as so-called fusion proteins.

The dye and the binding site are chosen in dependence on the biological analyte to be determined by the use of the device according to the invention or by carrying out the method according to the invention, and the assay to be used therefor.

It is possible to use all known fluorescent dyes which are otherwise also used in measurements of biological samples. Such dyes are, for example, cyanines, coumarins, fluoresceins, rhodamines and derivatives thereof, such as, for example, fluorescein isothiocyanate. They are available commercially (for example Alexa™, Dy-Light™, Atto™ or Oyster™).

In addition to the above-mentioned fluorescent dyes, fluorescent quantum dots ("Qdots") can also be used to produce fluorescence markers. Such fluorescence markers are distinguished by particularly high fluorescence emission.

It is conceivable that the biological analyte to be determined is itself coupled with a fluorescent dye and used as the fluorescence marker. Such fluorescence markers are suitable for competitive assays in which the fluorescence marker competes with the same, non-fluorescence-labelled biological analyte to bind to the catcher molecule.

In one embodiment of the invention, different fluorescence-labelled antibodies are used as the luminescence marker, so that different analytes or epitopes in different fluorescence channels can be detected simultaneously (multiplexing).

Unless indicated otherwise, the term "sample" is understood as meaning the following: fluid, buffer solutions of any kind, media for cell culture and for fermentations, as well as blood, blood plasma, urine, serum, all of which contain at least one type of biological analyte. Particularly suitable samples according to the invention are fluid, buffer solutions of any kind, media for cell culture and for fermentations.

Unless indicated otherwise, the expression "aqueous solution" is understood as meaning the following: An aqueous, preferably pH-buffered solution (for example a Tris buffer) in which (further) substances conventional in protein biochemistry, such as, for example, bovine serum albumin (BSA), detergents (for example Tween 20) or the like, are optionally present. The expression also includes reaction and binding buffers. Binding buffers are known and can be adapted to the particular test requirements.

Unless indicated otherwise, the expression "measuring solution" is understood as meaning an aqueous solution in which the test components are present in solution and/or suspension while the method according to the invention is being carried out.

Unless indicated otherwise, the expression "test component" is understood as meaning at least one of the following components: luminescence markers, functionalised stationary surfaces, functionalised particles, or functionalised magnetic particles, and sample as well as catcher molecules and primary antibodies.

The test components can be used in the method according to the invention in solution or suspension in a solvent, preferably in an aqueous solution. Likewise, the test components can be used in the method according to the invention in pure form, that is to say without the addition of a solvent. This is the case, for example, with a sample when it is fluid, buffer solutions or cell culture media, each of which contains at least one biological analyte. Preferred solvents are aqueous solutions as defined herein.

Unless indicated otherwise, a biological analyte according to the invention or the terms "analyte" and "analytes" is/are understood as meaning a molecule which is to be determined or detected by the method according to the invention. Examples of such biological analytes are proteins, antibodies, protein or antibody complexes, peptides, DNA, RNA, complexes of one or more biomolecules, viruses or one or more biological cells or constituents thereof, as well as low molecular weight substances which have biological activity or interact with biomolecules. Biological analytes which can be detected particularly well in the method according to the invention are: proteins, antibodies, protein or antibody complexes, peptides, DNA, RNA, complexes of one or more biomolecules, and viruses.

Unless indicated otherwise, the term "introduction" or "introduce" is understood as meaning the following: Manual or automatic filling of the device, or of the measuring chamber, by conventional measures such as, for example, pipetting or by the use of microfluidic systems.

Unless indicated otherwise, the term "binding" is understood as meaning that at least two units come into contact with one another so that a stable binding equilibrium is established between them. Such binding is generally mediated by interactions and results in the corresponding bonds, such as for example, hydrogen bonds, salt bonds, complex bonds and covalent bonds. The bonds utilised in the method and device according to the invention are often a mixture of several of the above-mentioned interactions.

Luminescence within the meaning of the invention includes all known types of luminescence, in particular fluorescence excited by light, bioluminescence and chemiluminescence, with fluorescence being preferred. In the fluorescence measurement, molecules are raised to an excited electronic state by excitation light and then return to the ground state by giving up the energy by emitting radiation (fluorescence radiation of one or more specific wavelengths or fluorescence). Measuring the fluorescence of molecules is an established method.

Unless indicated otherwise, the expression "magnetic element" is understood as meaning the following: Coating or magnetic layer, such as, for example, the foil Permaflex 518 from Rheinmagnet. The layer thickness and the foil is so selected that the magnetic strength of the foil allows the functionalised magnetic particles to sediment on the bottom of the device after mixing only outside the measuring window, while the measuring window remains free, but without interfering with the efficient mixing of the test components (preferably on a shaker). Suitable field or magnetic strengths are thus those which are weak enough to allow the test components to be mixed and strong enough to attract the magnetic particles after mixing, whereby the measuring window must be kept free of magnetic particles. Suitable magnetic foils are available commercially. The measuring windows are produced in the foil by punching or by laser cutting.

If Protein A Mag-Sepharose® particles (GE Healthcare Art. No. 28-9440-06) are used in combination with the foil Permaflex 518 from Rheinmagnet, a layer thickness of approximately 1 mm is advantageous.

Unless indicated otherwise, the following applies also to the methods according to the invention in which functionalised magnetic particles are used.

According to the invention, fluorescence markers are preferably used in the method according to the invention and the measurement in step (d) is a fluorescence measurement and is carried out with a fluorescence meter.

The device according to the invention and the method according to the invention allow a time-resolved, kinetic fluorescence measurement to be carried out. This is advantageous, for example, if the establishment of the binding/reaction equilibrium is to be monitored.

Step (e) in the method according to the invention, namely determining the quantity and/or concentration of the biological analyte or analytes, is carried out using a calibration series. For the calibration series, the method according to the invention is carried out with different, defined concentrations/quantities of the analyte which cover the desired or expected concentration range of the analyte, and in each case with identical test conditions, in particular the concentration of the luminescence marker. From the measured values of the luminescence emission of the unbound luminescence marker there is then produced a calibration curve, or a function, by means of which the analyte concentrations in samples of unknown analyte content are determined. Examples of such calibration curves are shown in FIGS. 5a to 5e. The above-mentioned calibration series and the preparation of calibration curves for determining values are conventional in biochemistry. A person skilled in the art knows how to prepare such a calibration curve in order to obtain meaningful results.

The method according to the invention determines the luminescence of the luminescence markers present in unbound form in solution. This is novel, because the known methods for determining biological analytes are based on measuring the luminescence markers bound to the biological analytes. If the fluorescence of unbound luminescence markers is measured in the prior art, the measurement is mostly preceded by an enzymatic reaction or a cleavage, in which a fluorescence marker is cleaved from a detection antibody, or is produced by FRET or particulate probes. Such a cleavage is not provided in the method according to the invention.

For determining the concentration of biological analytes by means of the method according to the invention, and if it is not a competitive assay, it is advantageous if as large a proportion as possible of the biological analytes is bound to the catcher molecules. This is facilitated by the fact that the catcher molecules are present in excess on the surface (preferably particle surface) and have a high affinity for the analyte. Ideally, the binding reaction of the analyte to the catcher molecules takes place completely.

In the above-mentioned case, the concentration of the unbound luminescence marker (for example fluorescence marker) is dependent only on the dissociation constant $K_d$ between the analyte and the luminescence marker (for example fluorescence marker), the concentration of the luminescence marker (for example fluorescence marker) that is used, and the concentration of the biological analyte that is to be determined.

If the concentration of the luminescence markers (for example fluorescence markers) is kept constant in the assay, the concentration of the unbound luminescence markers (for example fluorescence marker) and thus the measured luminescence intensity (for example fluorescence intensity) depends only on the concentration of the biological analyte.

For determining the concentration of the biological analytes by means of the method according to the invention and with a competitive assay, it is advantageous if the number of catcher molecules is smaller than or equal to the number of luminescence markers, so that each binding of an analyte molecule leads to an increase in the number of unbound luminescence markers.

In addition to determining the concentration of the analyte, further information about the binding of the analyte to the test components, for example the dissociation constant $K_d$, or IC or $EC_{50}$ values, can also be obtained with the method according to the invention.

By means of the method according to the invention using the device according to the invention, the determination, in particular the quantification, of the biological analytes can be carried out with a very simple, namely one-stage, assay protocol. Such one-stage assays are also called "mix-and-measure assays". In the method according to the invention, the test components are simply combined, and establishment of binding equilibrium is awaited.

After waiting for the sedimentation of the particles, the measurement can immediately be begun. Within a short time, normally in less than one hour, the desired data are obtained, which, after correlation with the calibration curve, yields the desired quantitative or qualitative result. Simple luminescence or fluorescence detection devices (fluorescence readers), as are often present in the laboratory, are sufficient for the measurement.

The method according to the invention can be configured as a non-competitive or competitive assay. Sandwich immunoassays with direct and indirect detection can also be carried out with the method according to the invention. Preferred assays to be carried out with the method according to the invention are the direct assay, sandwich assay with direct or indirect detection, displacement assay, competitive assay and secondary assay.

In the direct assay, the biological analyte is generally an antibody which is bound to a catcher molecule which is itself not an antibody but an antigen to which the antibody binds specifically with its variable portion (shown schematically in FIG. 6c) or protein A and G which bind the antibody at their Fc portion (shown schematically in FIG. 6a).

Figure 6D:
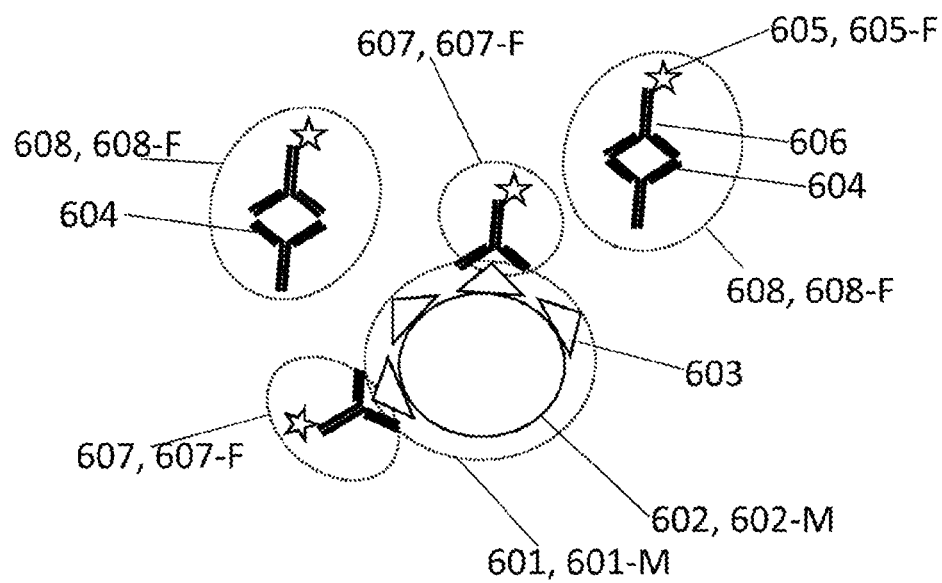

In an inhibition assay, that is to say displacement assay, the biological analyte wholly or partially prevents the luminescence marker from binding to the functionalised surface by binding to the binding site of the luminescence marker so that the binding site is no longer available for binding to the catcher molecules (shown schematically in FIG. 6d).

In the sandwich assay with direct detection, the biological analyte is generally a protein or an antibody which is bound by the variable portion of an antibody which acts as the catcher molecule, the luminescence marker, preferably fluorescence marker, binding to a second binding site (epitope) of the analyte and thus forming the sandwich (shown schematically in FIG. 7a).

In the sandwich assay with indirect detection, the biological analyte is generally a protein or an antibody which is bound by the variable portion of an antibody as catcher molecule, luminescence markers, preferably fluorescence markers, not binding directly to the analyte but to a further primary antibody, which binds to a second binding site (epitope) of the analyte (shown schematically in FIG. 7b).

In all the suitable assay variants, a defined quantity of functionalised surfaces and luminescence marker, preferably fluorescence marker, and optionally primary antibodies is introduced into the device or measuring chamber according to the invention.

In the competitive assay, a defined quantity of catcher molecules or functionalised surfaces, the sample and luminescence marker, preferably fluorescence marker, which competes with the analyte to bind to the same binding site (epitope) on the catcher molecules, are together introduced into the device or measuring chamber according to the invention. The reaction is carried out therein, with shaking, until the reaction equilibrium is established, and sedimentation of the particles is awaited. The quantity of unbound luminescence marker, preferably fluorescence marker, in the measuring solution is then measured and the concentration of the analyte is determined via a calibration curve or calibration function.

The concentration of the unbound luminescence marker, preferably fluorescence marker, is thereby dependent only on the quantity of the analyte, which wholly or partially prevents the luminescence marker, preferably the fluorescence marker, from binding to the catcher molecules and thus effects an increase in the fluorescence signal in the detection region.

The device according to the invention for use in the method according to the invention is so configured that it is capable of separating test components bound to functionalised surfaces and unbound test components. To that end, the device contains a structural element. The structural element is in particular in the form of a protrusion, the cross section of which can have any desired geometry (for example circular, rectangular, triangular), wherein the end that is remote from the base is such that no test components settle there when they are particles. The structural element advantageously has a protrusion on the base of the device which extends straight upwards or tapers, and is at least partly transparent. The end can have a convex shape, for example, and/or can have a small diameter. The structural element is preferably in the form of a cone, a truncated cone or a pyramid and protrudes from the base of the device. The structural element can further have an optical component, for example a lens, at the end that is remote from the base of the device. It preferably has the shape of a mandrel, cone or truncated cone. The structural element can be made of polypropylene and is transparent. Other geometric forms of a protrusion which fulfill the purpose described hereinbelow are conceivable.

The purpose of the structural element is to keep free the beam path provided in the method according to the invention for the detection of the luminescence and to prevent any luminescence of the bound luminescence markers that may falsify the result from reaching the measuring device. The presence of a structural element for separation is important because the biological analytes are determined via the luminescence of the luminescence markers that are present in unbound form. It is at least partly transparent.

The device according to the invention likewise has a region which serves as a measuring window. The measuring window can be present in the base of the device or at the end of the device that is opposite the base. The base of the at least partly transparent structural element can be a measuring window. Excitation and detection usually take place through the measuring window. It is, however, also possible that the measuring window is used only for detection. The configuration and the position of the measuring window inside the device or measuring chamber can vary and be adapted to the requirements of the measurement. It is important, however, to ensure that only the luminescence of the luminescence markers present in unbound form is measured through the measuring window. The sensitivity of the method in which the device is used can be modulated by suitably selecting the size of the measuring window and the type of luminescence marker.

The region within the device or measuring chamber in which the luminescence markers emit luminescence and which can be observed/measured spectroscopically through the measuring window is called the "measuring region" or "detection region" hereinbelow.

The region within the device or measuring chamber which cannot be observed/measured spectroscopically through the measuring window is referred to as the "separation region" hereinbelow.

In the device according to the invention, the detection region and the separation region are connected, so that the test components can effectively and easily be exchanged between the two regions. The concentration of the unbound luminescence marker is thus the same throughout the device/measuring chamber.

In a preferred embodiment of the invention, the measuring window is optically connected to the end of the structural element that is remote from the base and represents the base area of the structural element. For example in that the structural element constitutes a protrusion on the base of the device which extends straight upwards or tapers and is transparent, and the base of the device has an opaque layer or coating, the base area of the structural element not being coated. The opaque layer (for example a black lacquer layer) is so applied that a region on the base of the device that is situated beneath the structural element is kept free, whereby the measuring window is formed.

If light is then directed into the measuring chamber from the base of the device, the radiation runs through the structural element into the measuring region. After excitation of the luminescence markers in the measuring region, the emission can be measured again at the measuring window.

In a further embodiment of the method there can be used a device, measuring chamber or microplate according to the invention, in particular as described above or in one of embodiments [0], [A], [B], [C], [D], [E], [F] or [G], that does not have an opaque layer, namely when the fluorescence meter used is a fluorescence microscope in which the measuring optics is so adapted that only the fluorescence emission from the detection region is detected, for example by choosing an optics with suitable imaging properties and a suitable collection efficiency (for example automated fluorescence microscope of type NyONE (SynenTec, Elmshorn, Germany) incl. 10×objective from Olympus).

If functionalised particles are used as the functionalised surfaces in the device according to the invention and in the method according to the invention, separation of the unbound luminescence markers from particle-bound luminescence markers usually takes place by sedimentation. To that end, the device loaded with measuring solution is not moved for a certain time. The functionalised particles with luminescence markers bound thereto have a higher density than the surrounding measuring solution and sediment. The unbound luminescence markers remain in solution. The bound luminescence markers then settle on the base of the device around the structural element, so that they are situated in the separation region. If functionalised (magnetic) particles are used in the method according to the invention, it accordingly comprises also step (c'), namely allowing the device to stand for a certain time, preferably for from 1 to 30 minutes or from 1 to 20 or from 1 to 15 minutes, particularly preferably for from 1 to 10 minutes, or, when magnetic particles are used, for from 1 to 5 minutes, particularly preferably for from 1 to 2 minutes.

Generally, if functionalised magnetic particles are used, the sedimentation time of the bound luminescence markers is less than 5 minutes. If magnetic particles are not used, the sedimentation time is less than 30 minutes, usually in the range of from 5 to 20 minutes.

If it is desired to perform a test quickly, it is advantageous to use functionalised particles which have a high density. In the case of non-magnetic particles, an average diameter of approximately 90 µm has been found to be advantageous.

In this connection, high density means that the (magnetic) particles used have a higher density than the aqueous test solution.

If non-magnetic particles which are smaller than 1 µm are used in the method according to the invention, it is advantageous, instead of waiting for the particles to sediment, to insert a centrifugation step before the luminescence measurement, whereby the particles are brought onto the base of the device.

It is likewise advantageous for performing a test quickly if the (magnetic) functionalised particles have a large surface area, as a result of which there is a high probability that a biological analyte will come into contact with a catcher molecule as it diffuses through the solution. The probability is increased by shaking (agitating) the device.

The device can be combined with known laboratory devices and consumables, for example with microplates and Eppendorf test tubes, or other vessels and plates, in order to be able to carry out the method according to the invention therewith. The side walls of the above-mentioned equipment then form, together with the device according to the invention, a measuring chamber. Advantageously, a plurality of measuring chambers of the same type (for example in the form of a microplate) are accommodated in a holder system, it being advantageous if the dimensions comply with the standard of the "Society for Biomolecular Screening" (SBS) of 127.76 mm×85.48 mm×14.35 mm, in order to be able to work on devices which are conventional in the laboratory and thus to be able to achieve a high degree of automation.

In one embodiment of the invention, the invention relates to a measuring chamber, consisting of a chamber which is open or closed at the top, which has side walls and the base of which is formed by the device. The measuring chamber can have round or straight side walls. It is, however, also possible that the measuring chamber has a plurality of bases, namely when the base of the device is present in addition to the base of the measuring chamber.

The side walls of the measuring chamber and the base of the device, or the side walls of the measuring chamber and another base on which the device is situated, are preferably connected, for example bonded or welded, in such a manner that they are impermeable to liquids.

In a further embodiment of the invention, the device is introduced into the well of a microplate, the edges of the well then forming the side edges of the measuring chamber.

In a further embodiment of the invention, the invention relates to a microplate in which the original bottom of the microplate has been replaced by a one-piece base containing the structural elements, that base, apart from the base area of the structural elements, being coated in such a manner that it is opaque (for example by adhesive bonding of an opaque foil with corresponding apertures, or by painting).

The production of the device in the above-mentioned SBS format is carried out, for example, by using a microplate without a bottom and applying in place of the bottom a transparent and non-fluorescent foil (for example of polypropylene), in which the structural elements are embossed in the arrangement corresponding to the SBS format. Such foils represent a plurality of one-piece devices. The structural elements then point into the openings in the microplate. Such embossed foils are available commercially (for example Arraytape™ from Douglas Scientific).

Application of the foil to the side of the microplate on which the bottom would actually be situated is usually carried out by adhesive bonding with an adhesive which is capable of bonding two different plastics materials. Most simply, a UV-curing adhesive which is not fluorescent is used for that purpose. Finally, an opaque non-fluorescent lacquer layer is applied to the underside of the plastics foil in such a manner that the underside is kept free in the region of the structural elements. It is also conceivable that the lacquer layer is first applied to the foil and then the foil is adhesively bonded to the microplate.

The production of the microplates with magnetic elements is carried out by bonding a commercial microplate having a transparent bottom (also called a "base" in this context) in an optionally reversible, that is to say permanently connected or detachable manner, to a magnetic foil of a suitable magnetic strength, which foil has an aperture for each well (which corresponds to the measuring chamber) of the microplate, which aperture is used as the measuring window. The apertures are so arranged that, when the foil is bonded to the bottom of the microplate, they are situated centrally beneath the wells of the microplate. The optimal size of the aperture depends on the size of the well and can be determined by a person skilled in the art on the basis of the following example. The diameters of the apertures must correspond to the dimensions of the wells and the number and size of the particles which are used in the assay. In the case of a 384-well microplate, apertures having a diameter of approximately 2.5 mm have been found to be advantageous in the case of the use of approximately 1000 magnetic particles per well. This corresponds to approximately half the bottom area of a commercial 384-well plate and on the one hand provides a sufficient surface for separation of the magnetic particles and at the same time provides a sufficiently large measuring window for the fluorescence measurement.

Owing to the particular configuration of the device or of the measuring chamber, the bound luminescence markers or fluorescence markers, which sediment and thus migrate out of the detection region, are not excited to luminescence or fluorescence. The invention will be explained with reference to the examples depicted hereinbelow in the figures and described in the following, without limiting the invention thereto.

FIG. 1a: Vertical section through a measuring chamber (101) having a structural element.

FIG. 1a shows a measuring chamber (101) consisting of a one-piece device (102) having a structural element (103) which has a measuring window (104) through which excitation light (105) passes into the detection region (106) and through which the emission of the luminescence (107) is measured with a suitable detection device, which at the same time also supplies the excitation light, or detection unit. The one-piece device (102) is connected to the side walls (108) in a liquid-impermeable manner. On the lower side of the base of the device there is an opaque layer (109) (for example lacquer or foil), the base area of the structural element (110) being kept free.

Figure 1B:
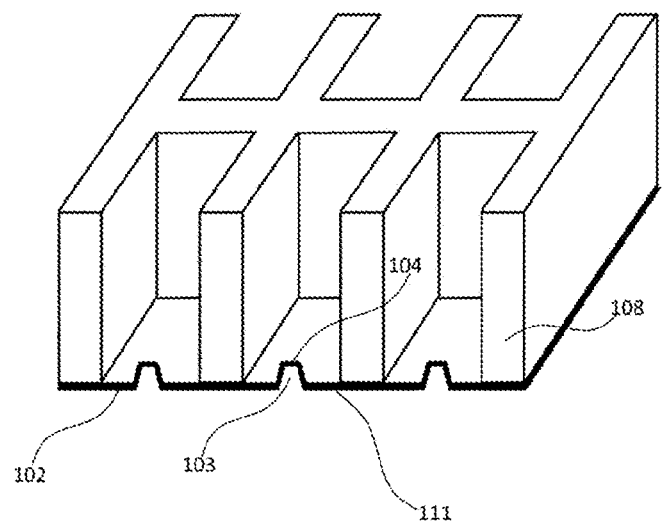

FIG. 1b: Vertical section through a sequence of devices as can be integrated, for example, into a microplate.

FIG. 1b shows a plurality of devices (102) which are introduced into the cups/wells of a microplate, the side walls (108) belonging to the microplate and the device being a foil (111) into which the structural elements (103) are embossed.

Figure 1C:
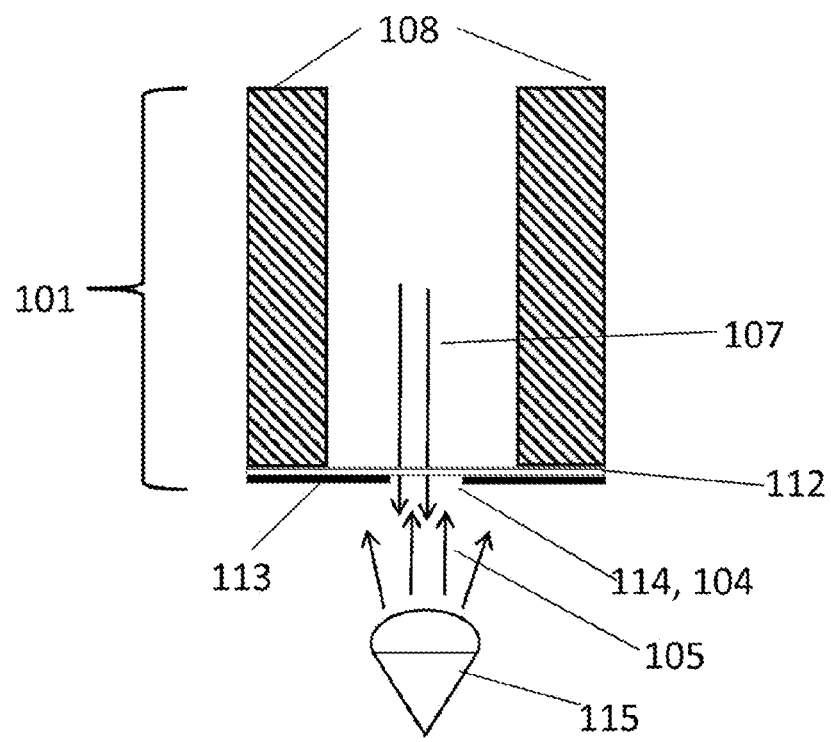

FIG. 1c: Vertical section through a measuring chamber (101) having a magnetic element.

FIG. 1c shows a measuring chamber (101), open at the top, consisting of a transparent base (112), there being situated beneath the base an opaque magnetic element (here: an opaque magnetic layer or foil) (113) having an aperture (114), the aperture (114) forming the measuring window (104). Excitation light (105) passes through the measuring window (104) into the measuring chamber from beneath (that is to say from the base of the device), causing emission of the luminescence (107) of the unbound luminescence markers, which is then detected through the measuring window (104) beneath the device by means of the detection unit (115). Advantageously, and as shown, the detection unit (for example a fluorescence reader) is able to emit excitation light and detect the luminescence. The base (112) is connected to the side walls (108) and to the magnetic element (113) removably or non-removably. The base and the side walls are made of the same or different materials.

Figure 1D:
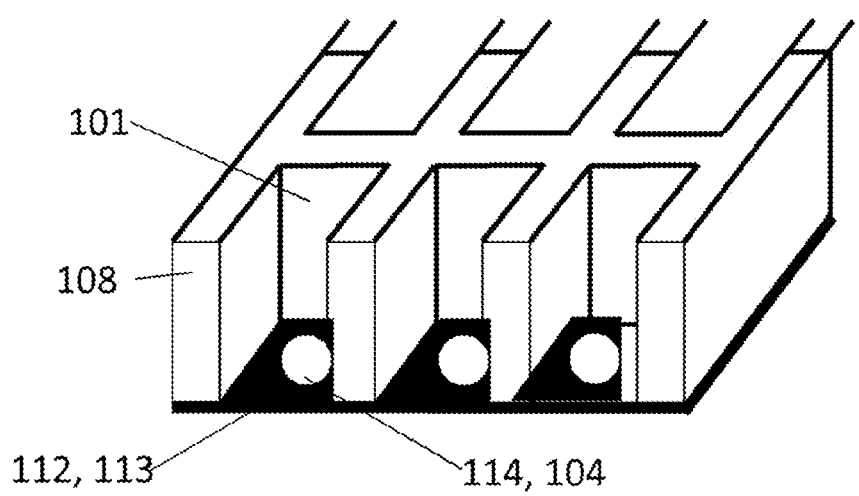

FIG. 1d: Vertical section through a sequence of measuring chambers (101) (for example in the form of a microplate).

FIG. 1d shows a plurality of measuring chambers (101) as well as the transparent base (112) and the opaque magnetic layer or foil (113) with an aperture (114), which serve as measuring windows (104). Excitation in the method according to the invention and also detection take place through the measuring window from beneath, that is to say from beneath the base of the plurality of measuring chambers, or microplate.

Figure 2A:
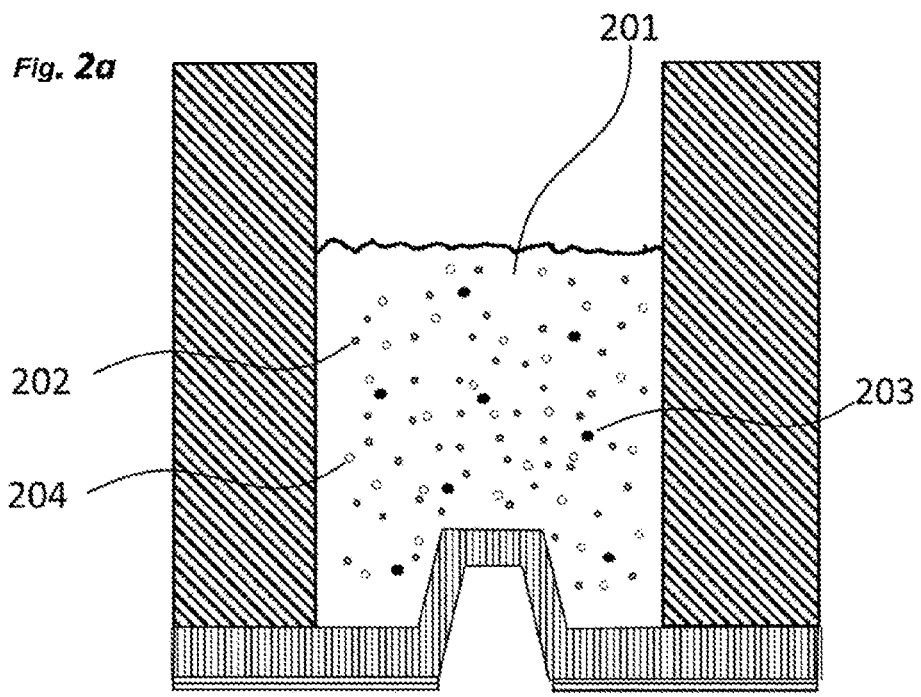

FIG. 2a: Vertical section through the measuring chamber of FIG. 1a with measuring solution, after filling of the device but before binding-schematic representation.

FIG. 2a shows the measuring chamber from FIG. 1a filled with measuring solution (201), comprising the following test components: biological analyte (204), functionalised particles (203) and luminescence markers (202) immediately after introduction, homogeneously distributed and in the unbound state before contacting by mixing. The functionalised particles can also be magnetic (not depicted here).

Figure 2B:
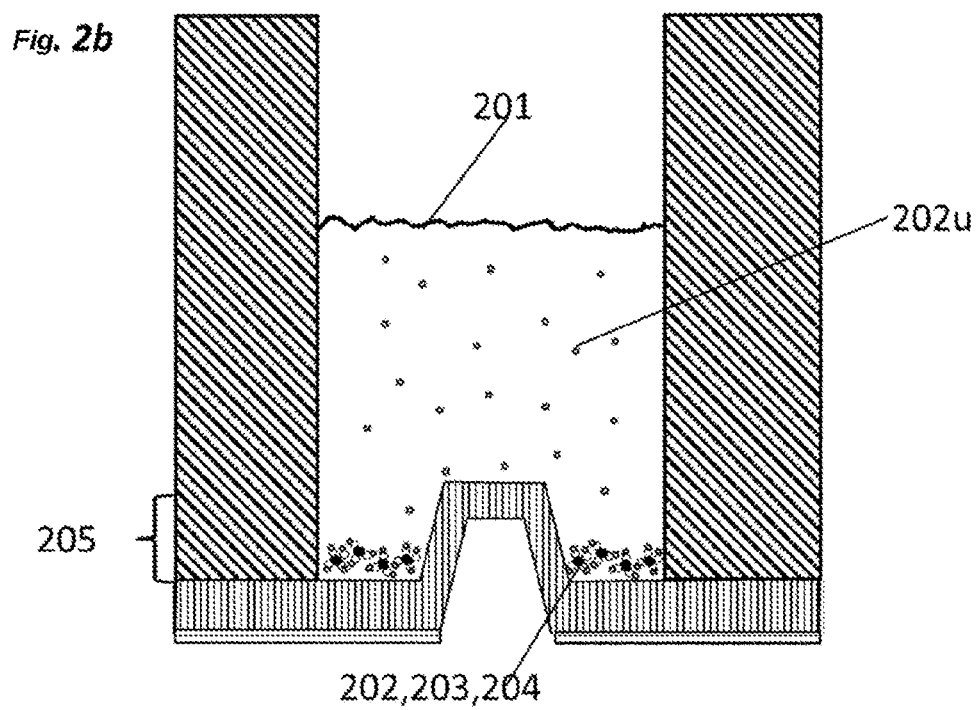

FIG. 2b: Vertical section through the measuring chamber of FIG. 1a with measuring solution, after filling of the device, binding and separation-schematic representation.

FIG. 2b shows the measuring chamber from FIG. 2a filled with measuring solution (201), comprising the test components (202), (203), (204) after binding and separation of the bound luminescence markers from the unbound luminescence markers. The unbound luminescence markers (202u) are homogeneously distributed in the measuring chamber, while the bound test components (202, 203, 204) are in the separation region (205).

Figure 2C:
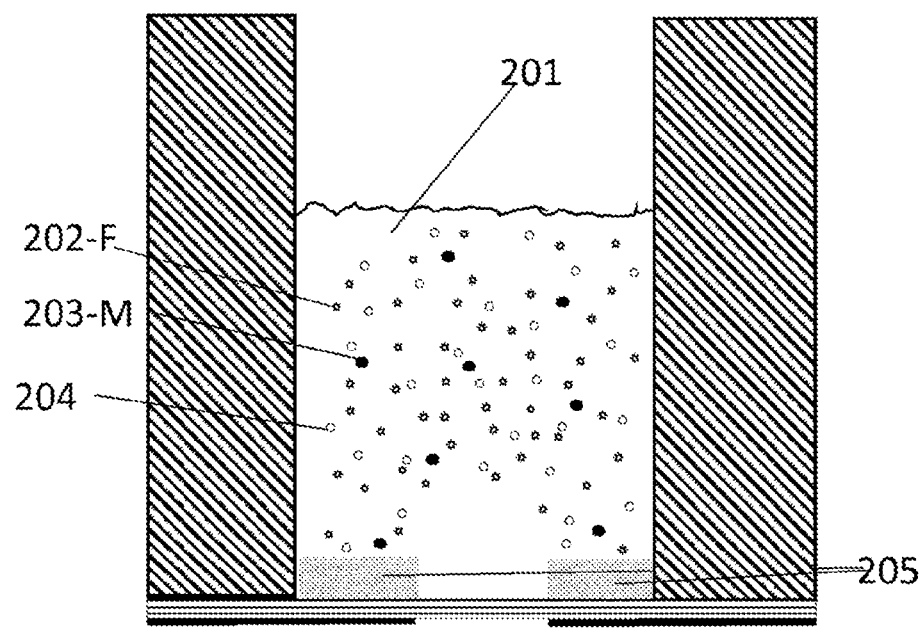

FIG. 2c: Vertical section through the measuring chamber of FIG. 1c with measuring solution, after filling of the device but before binding-schematic representation.

FIG. 2c shows the measuring chamber of FIG. 1c filled with measuring solution (201), comprising the following test components: biological analyte (204), functionalised magnetic particles (203-M) and fluorescence markers (202-F) immediately after introduction, homogeneously distributed and in the unbound state before contacting by mixing.

Figure 2D:
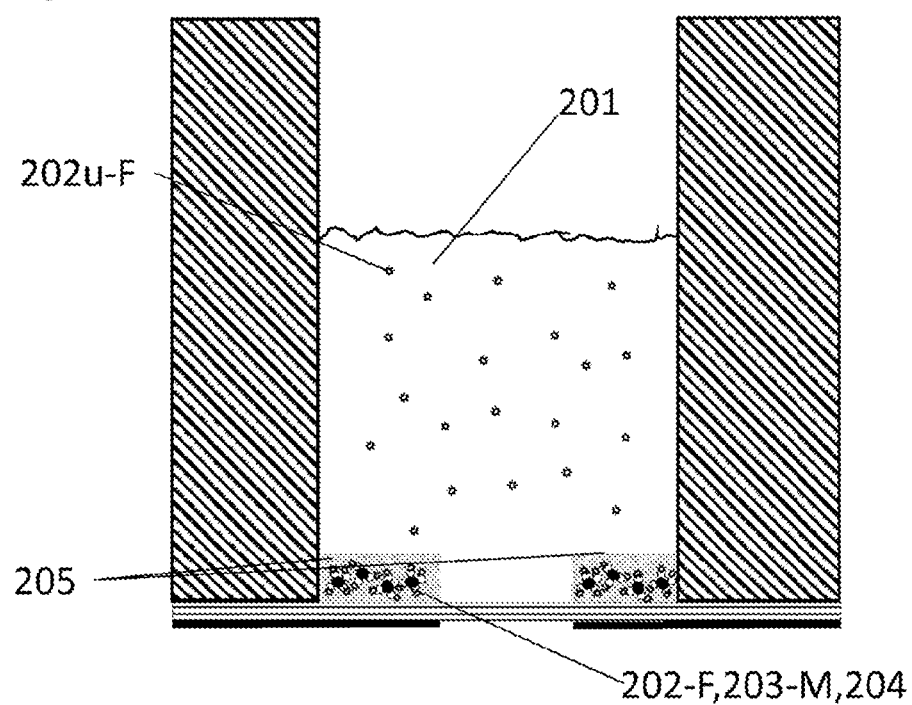

FIG. 2d: Vertical section through the measuring chamber of FIG. 1c with measuring solution after filling of the device, binding and separation-schematic representation.

FIG. 2d shows the measuring chamber of FIG. 2c filled with measuring solution (201), comprising the test components (202-F), (203-M), (204) after binding and separation of the bound fluorescence markers from the unbound fluorescence markers. The unbound fluorescence markers (202u-F) are distributed homogeneously in the measuring chamber, while the bound test components (202-F, 203-M, 204) are in the separation region (205).

FIG. 3a: Top view into the measuring chamber of FIG. 2b after filling of the device, binding and separation-schematic representation.

FIG. 3a is a top view of the measuring chamber of FIG. 2b. The bound test components (301) are situated on the base of the device/measuring chamber. The base of the device is provided with an opaque layer (302), the base area of the structural element (303) being kept free. The aperture at the same time represents the measuring window (305). Also depicted is the end (304) that is remote from the base of the device, which end is optically connected to the measuring window (305). The structural element is here an upwardly tapering protrusion with a round cross section.

FIG. 3b: Top view into the measuring chamber of FIG. 2d after filling of the device, binding and separation-schematic representation.

FIG. 3b is a top view of the measuring chamber of FIG. 2d. The bound test components (301) are situated on the base of the measuring chamber. The base of the measuring chamber is provided with an opaque magnetic layer or foil (306) with an aperture (307). The aperture at the same time represents the measuring window (305).

FIG. 4: Top view of a 384-well microplate (401) containing a plurality of measuring chambers (402).

Figure 5A:
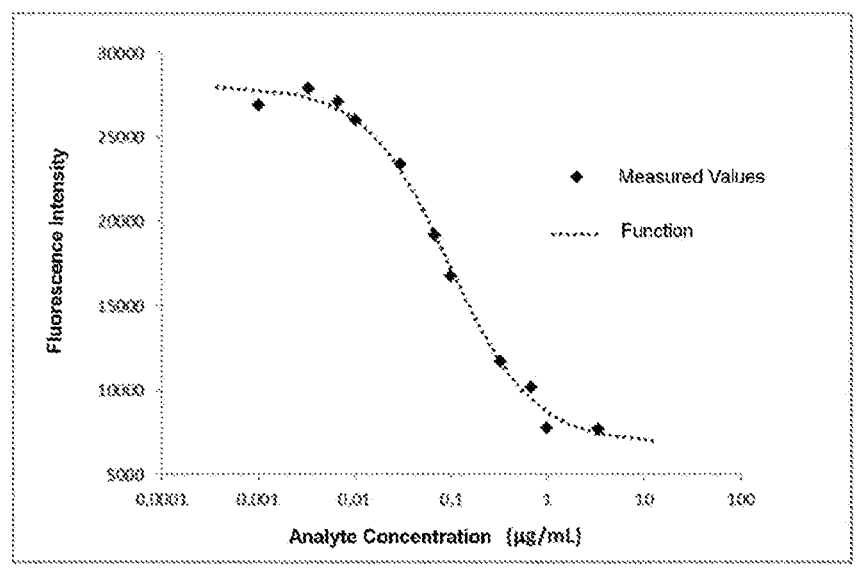
Figure 5B:
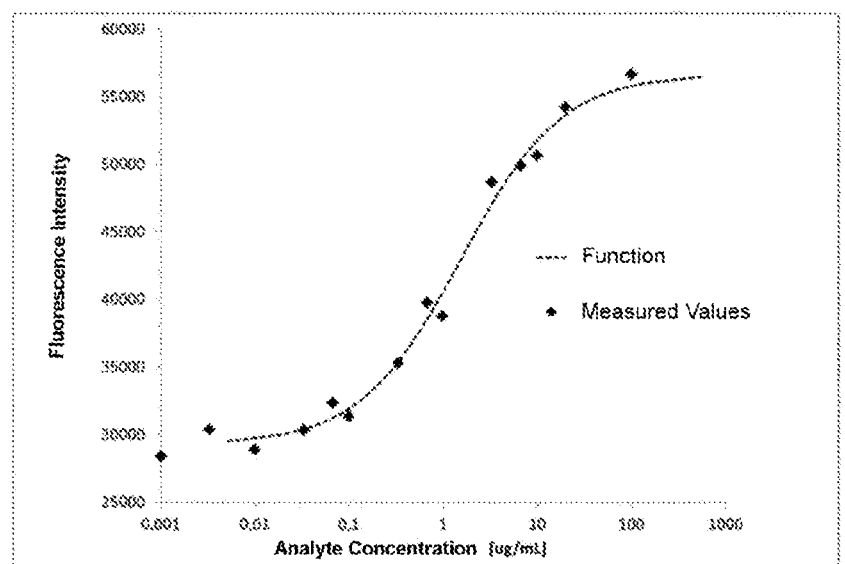
Figure 5C:
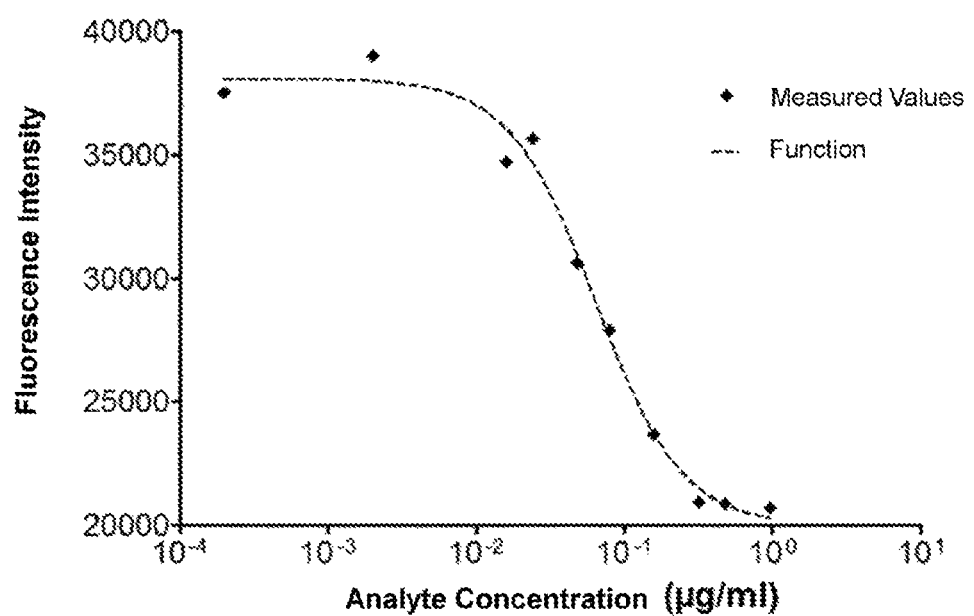

FIG. 5a: Calibration curve from Example A.
FIG. 5b: Calibration curve from Example B.
FIG. 5c: Calibration curve from Example C.

In FIGS. 5a, 5b and 5c, the analyte concentration in µg/ml is represented on the x-axis and the fluorescence intensity is represented on the y-axis. A function is drawn (dotted line) through the measured values (as diamonds).

Figure 5D:
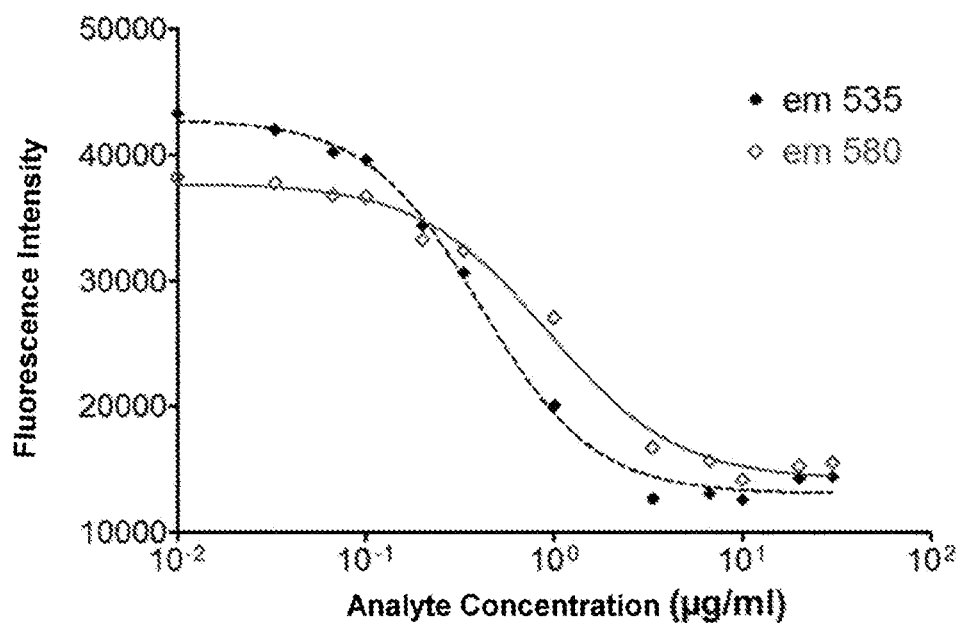

FIG. 5d: Measurement with two fluorescence markers from Example D.

In FIG. 5d, the analyte concentration in µg/ml is represented on the x-axis and the fluorescence intensity for two fluorescence markers which bind to different epitopes of the same analyte is represented on the y-axis. The fluorescence markers emit at two different wavelengths (535 and 580 nm). The corresponding functions are drawn (dotted line) through the measured values (each as diamonds).

Figure 5E:
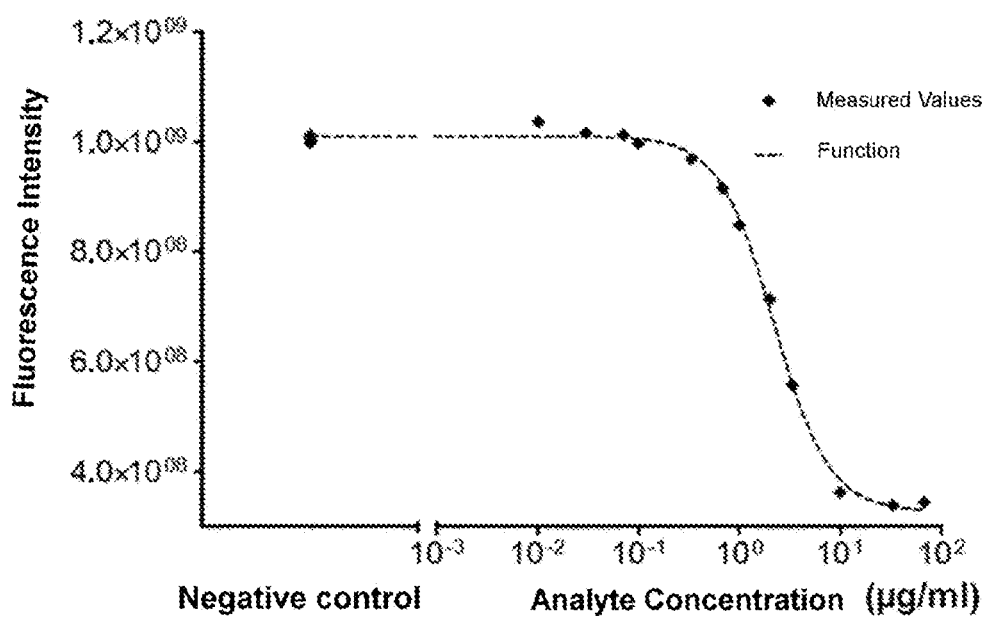

FIG. 5e: Measurement of an assay in a microplate without a transparent layer from Example E.

In FIG. 5e, the analyte concentration in µg/ml is represented on the x-axis and the fluorescence intensity is represented on the y-axis. A function is drawn (dotted line) through the measured values (as diamonds). Since this example was measured with a fluorescence microscope, the scaling of the y-axis is different than in the preceding examples.

FIG. 6a: Schematic representation of the binding behaviour of the test components in a direct immunoassay for antibodies having a catcher molecule which binds the Fc portion of the antibody.

FIG. 6a shows a functionalised particle (601), or functionalised magnetic particle (601-M), consisting of a particle (602), or magnetic particle (602-M), on which a plurality of catcher molecules (603) are present. The biological analytes (604) bind to the catcher molecules (603) and the luminescence marker (607), or fluorescence marker (607-F). Also present are unbound luminescence markers (607u), or unbound fluorescence markers (607u-F). The luminescence marker, or fluorescence marker, has a binding site (606) and a luminescent dye (605), or fluorescent dye (605-F).

FIG. 6b: Schematic representation of the binding behaviour of the test components in a competitive immunoassay.

FIG. 6b shows a functionalised particle (601), or functionalised magnetic particle (601-M), consisting of a particle (602), or magnetic particle (602-M), on which a plurality of catcher molecules (603) are present. The catcher molecules (603) bind either to the biological analyte (604) or to the luminescence marker (607), or fluorescent marker (607-F), the biological analyte (604) being capable of displacing the bound luminescence marker, or bound fluorescence marker, from the catcher.

FIG. 6c: Schematic representation of the binding behaviour of the test components in a direct immunoassay for antibodies having an antigen as catcher molecule, to which the variable portion of the antibody binds.

FIG. 6c shows a functionalised particle (601), or functionalised magnetic particle (601-M), consisting of a particle (602), or magnetic particle (602-M), on which a plurality of catcher molecules (603) are present. The biological analytes (604) bind to the catcher molecules (603) and the luminescence marker (607), or fluorescence marker (607-F). Also present are unbound luminescence markers (607u), or unbound fluorescence markers (607u-F). The luminescence marker has a binding site (606) and a luminescent dye (605), or fluorescent dye (605-F).

FIG. 6d: Schematic representation of the binding behaviour of the test components in an inhibition assay for antibodies.

FIG. 6d shows a functionalised particle (601), or functionalised magnetic particle (601-M), consisting of a particle (602), or magnetic particle (602-M), on which a plurality of catcher molecules (603) are present, the catcher molecules (603) being able to bind the fluorescence marker (607-F), consisting of binding site (606) and fluorescent dye (605-F). The biological analyte (604) binds to the fluorescence marker (607-F) and thereby prevents (inhibits) binding of the fluorescence marker to the catchers (603). In this type of binding, the complex (608, 608-F) is detected, namely the luminescence marker (607), or fluorescence marker (607-F), bound to the biological analyte (604).

FIGS. 7a and 7b: Schematic representation of the binding behaviour of the test components in a sandwich immunoassay with direct detection (FIG. 7a) and indirect detection (FIG. 7b).

Both figures show a functionalised particle (701), or functionalised magnetic particle (701-M), which consists of a particle (702), or magnetic particle (702-M), to which a plurality of catcher molecules (703) are bound. The catcher molecule is formed by a suitable protein (705), for example biotinylated antibody, which is bound to the particle (702), or magnetic particle (702-M), via a linker (704) (for example streptavidin). The protein (705) binds the biological analyte (709). Also depicted are bound luminescence markers (706), or bound fluorescence markers (706-F), and unbound luminescence markers (706u), or unbound fluorescence markers (706u-F). The luminescence marker (706), or fluorescence marker (706-F), has a binding site (707) and a luminescent dye (708), or fluorescent dye (708-F).

In FIG. 7b there is present, in addition to the test components shown in FIG. 7a, additionally also a primary antibody (710) which binds to the analyte (709) and to which the luminescence marker (706), or fluorescence marker (706-F), binds.

The method according to the invention can be carried out using the measuring chamber according to the invention as shown in FIG. 1a as follows:

A measuring solution (201) which comprises biological analytes (204), functionalised particles (203) and unbound luminescence markers (202) is introduced into the measuring chamber (101) (see FIG. 2a). A homogeneous mixture forms. After the corresponding bonds have formed (by incubation and shaking), the bound test components sediment into the separation region (205), where they collect (see FIGS. 2b and 3a). The unbound luminescence markers (202u) can now be measured in the detection region (105). The opaque layer (109) ensures both that the bound luminescence markers situated in the separation region cannot be excited to emission by excitation light and that the emission light of the bound luminescence markers cannot reach the detection unit/device from the measuring chamber through the measuring window.

The method according to the invention can be carried out using the measuring chamber according to the invention having magnetic elements, as shown in FIG. 1c, as follows:

A measuring solution (201) which comprises biological analytes (204), functionalised magnetic particles (203-M) and unbound fluorescence markers (202-F) is introduced into the measuring chamber (101) (see FIG. 2c). A homogeneous mixture forms. After the corresponding bonds have formed (by incubation and shaking), the bound test components, directed by the magnetic field of the magnetic element, sediment into the separation region (205), where they collect (see FIGS. 2d and 3b). The unbound fluorescence markers (202u-F) can now be measured in the detection region. The opaque magnetic layer or foil (113) ensures both that the bound fluorescence markers (202-F) situated in the separation region cannot be excited to emission by the excitation light and that the emission light of the bound fluorescence markers (202-F) cannot reach the detection device (115) from the measuring chamber through the measuring window (104).

Examples of calibrations for the method according to the invention which are carried out are described below. The determination of the biological analyte used in the calibration series takes place analogously to following examples on samples of unknown analyte content, the analyte concentration being determined via the measured fluorescence intensity of the unbound fluorescence markers using the respective calibration curve.

EXAMPLE A

Measurement of a Calibration Series in the Direct Assay Variant

The following microplate according to the invention is used for the measurement: A black microplate (Greiner BioONE, Art. No. 781000-06) with 384 wells (measuring chambers), in each of which there is situated a 1.6 mm high conical structural element of polypropylene which tapers upwards and has a round cross section and which has a diameter of 1 mm on the side that is remote from the base. The measuring chambers are provided on their underside with an opaque lacquer layer, wherein the layer is not applied to the base area of the structural element so that a measuring window having a diameter of approximately 2 mm is formed on the base.

There are used as the functionalised particles Protein A-Sepharose® 4B, Fast Flow beads (Sigma-Aldrich, Art. No. P9424) with an average diameter of 90 μm.

There is used as the fluorescence marker an Alexa 647-conjugated antibody fragment (Jackson Immuno Research, AffiniPure F(ab')$_2$ Fragment Goat Anti-Human IgG F(ab')$_2$ specific Art No. 109-606-097).

The following buffer is used as the aqueous solution: 10 mM Tris, 150 mM NaCl, 0.1% bovine serum albumin (BSA), 0.05% Polysorbate 20 (Tween 20™), pH 7.4 in distilled water (called buffer hereinbelow). The recombinantly produced antibody rituximab (Mabthera™) is used as the biological analyte for the calibration.

In the microplate, a calibration curve is prepared with a total of 12 different analyte concentrations. The analyte concentrations are 0/0.001/0.0033/0.0067/0.01/0.03/0.67/0.1/0.33/0.67/1.0 and 3.33 μg/ml rituximab (Mabthera™).

The procedure is as follows: 54 μl of a stock solution comprising 15 μl of Protein A Sepharose beads slurry and 60 μl of fluorescence marker (10 μg/ml) in 810 μl of buffer are added to each measuring chamber.

From a concentrated stock solution of the analyte (10 mg/ml), dilutions of from 1:300 to 1:1,000,000 in buffer are prepared and [aliquots of] in each case 6 μl thereof are added to the measuring chambers in order to achieve the target concentrations of analyte for the calibration series.

The entire microplate is shaken at 1400 rpm on an Eppendorf Thermomixer Comfort for 45 minutes at room temperature. The microplate is then removed from the thermomixer, and a period of 5 minutes is allowed to elapse until the particles have sedimented.

The fluorescence intensity in each measuring chamber is then measured from beneath (bottom reading) in a Tecan Infinite M100 fluorescence plate reader at an excitation wavelength of 645 nm and an emission wavelength of 675 nm.

The values obtained for the fluorescence intensity are plotted against the analyte concentrations and fitted using a 4 parameter fit in order to obtain the calibration function. The corresponding calibration curve is shown in FIG. 5a.

EXAMPLE B

Measurement of a Calibration Series in a Competitive Assay

The following microplate according to the invention is used for the measurement: A black microplate (Greiner BioONE, Art. No. 781000-06) with 384 wells (measuring chambers), in each of which there is situated a 1.6 mm high conical structural element of polypropylene which tapers upwards and has a round cross section and which has a diameter of 1 mm on the side that is remote from the base. The measuring chambers are provided on their underside with an opaque lacquer layer, wherein the layer is not applied to the base area of the structural element so that a measuring window having a diameter of approximately 2 mm is formed on the base.

There are used as the functionalised particles Streptavidin Mag-Sepharose® particles (VWR, Art. No. 28-9857-38) having an average diameter of 70 μm, which are functionalised with a biotinylated protein A fragment (Affibody, Art. No. 10.0623.02.00005). The particles are functionalised by incubating 100 μl of particle suspension for half an hour with 0.3 μl of a solution of the biotinylated protein A fragment having a concentration of 1 mg/ml and then washing the particles with buffer.

There is used as the fluorescence marker an Alexa 488-conjugated polyclonal rabbit anti-chicken IgY (H+L)-Alexa Fluor 488 (Jackson Immuno Research, Art. No. 303-545-003).

The following buffer is used as the aqueous solution: 10 mM Tris, 150 mM NaCl, 0.1% bovine serum albumin (BSA), 0.05% Polysorbate 20 (Tween™ 20), pH 7.4 in distilled water (called buffer hereinbelow). The recombinantly produced antibody rituximab (Mabthera™) is used as the biological analyte for the calibration.

In the microplate, a calibration curve is prepared with a total of 14 different analyte concentrations. The analyte concentrations are 0.001/0.0033//0.01/0.03/0.67/0.1/0.33/0.67/1.0/3.33/6.67/10/20 and 100 μg/ml rituximab (Mabthera™).

The procedure is as follows: Loading the measuring chamber with functionalised particles by adding to each measuring chamber 48 μl of a stock solution comprising 80 μl of a suspension of the above-mentioned functionalised particles in 1840 μl of buffer.

Preparing mixtures of fluorescence marker in each case in equal concentrations and biological analyte in different concentrations by preparing from a concentrated stock solution of the analyte (10 mg/ml) dilutions of from 1:10 to 1:1,000,000 in buffer. 6 μl aliquots of each of the dilutions are combined with 6 μl of the rabbit anti-chicken IgY (H+L)-Alexa Fluor 488 antibody (from a stock solution of 10 μg/ml) and mixed.

Introducing the mixture of fluorescence marker and biological analyte into the measuring chamber. Mixing the test components by shaking the microplate at 1600 rpm on an Eppendorf MixMate for 30 minutes at room temperature. When the shaking is ended, the microplate is removed from the shaker, and sedimentation of the particles is awaited, which here took approximately from 1 to 2 minutes.

Transferring the plate to a fluorescence recording device which is suitable for bottom reading (for example Tecan Safire Monochromatic Fluorescence reader), in which each measuring chamber is illuminated from beneath at a certain excitation wavelength (here 488 nm) and the resulting fluorescence emission or fluorescence intensity is recorded at a certain emission wavelength (here 535 nm).

Plotting the values obtained for the fluorescence intensity against the analyte concentrations and fitting using a 4 parameter fit in order to obtain the calibration function. The corresponding calibration curve is shown in FIG. 5b.

EXAMPLE C

Measurement of a Calibration Series in a Microplate Having a Magnetic Element

The following microplate according to the invention is used for the measurement: A black microplate having a transparent bottom (Greiner BioONE, Art. No. 781091) with 384 wells, beneath which a magnetic foil having 384 apertures is adhesively bonded so that each aperture is centred beneath a well of the microplate. The permanently magnetic foil (Permaflex 518, Rheinmagnet) has a thickness of 1 mm and the apertures have a diameter of 2.5 mm.

There are used as the functionalised magnetic particles Protein A Mag-Sepharose® particles (GE Healthcare Art. No. 28-9440-06) having a diameter of 37-100 µm.

There is used as the fluorescence marker a fluorescein isothiocyanate (FITC)-conjugated polyclonal chicken anti-human IgG (H+L) antibody (Abcam, Art. No. 112453).

The following buffer is used as the aqueous solution: 10 mM Tris, 150 mM NaCl, 0.1% bovine serum albumin (BSA), 0.05% Polysorbate 20 (Tween™ 20), pH 7.4 in distilled water. The antibody rituximab (Mabthera™) is used as the biological analyte.

The assay was carried out as described in Example A, the following stock solution comprising particles and fluorescence marker being used: 75 µl of a suspension of Protein A Mag-Sepharose® particles and 1.86 µl of the fluorescence marker in 1782 µl of buffer.

47 µl of the suspension were incubated for 30 minutes on a Variomag Monoshake (H+P) shaker with in each case 3 µl of a sample from the calibration series of rituximab. The microplate was then allowed to stand for 5 minutes in order to await sedimentation of the particles, and the measurement was then carried out.

Measurement is carried out in a Tecan Safire fluorescence reader at an excitation wavelength of 490 nm and an emission wavelength of 535 nm.

The calibration function is determined as described in Example A, and the corresponding calibration curve is shown in FIG. 5c.

EXAMPLE D

Measurement with Two Fluorescence Markers

The following microplate according to the invention is used for the measurement: A black microplate (Greiner BioONE, Art. No. 781000-06) with 384 wells (measuring chambers) and a one-piece bottom containing structural elements, which was produced by thermoforming. The structural elements have the shape of a four-sided square-based pyramid. The measuring chambers are provided on their underside with an opaque lacquer layer, wherein the layer is not applied to the square base area of the structural element so that a measuring window having a diameter of approximately 2.5 mm is formed on the base.

This assay is carried out using particles which were placed in the microplates in the already dried state. To that end, 30 µl of a suspension of Protein A-Sepharose® 4B Fast Flow beads are dried on the microplate at 35 degrees Celsius. A stock solution of 1.6 µl of a first fluorescence marker, namely Alexa 488 AffiniPure F(ab')₂ Fragment Goat Anti-Human IgG, F(ab')₂ specific (Jackson Immuno Research Art. No. 109-546-097), and 3.93 µl of a second fluorescence marker, namely R-Phycoerythrin AffiniPure F(ab')₂ Fragment Goat Anti-Human IgG, Fcγ Fragment specific (Jackson Immuno Research Art. No. 109-116-170), in 1607 µl of buffer are prepared, and in each case 54 µl thereof are incubated for 30 minutes on a Vario-mag Monoshake shaker (H+P) with in each case 6 µl of a sample from the calibration series of rituximab (Mabthera™). The microplate was then allowed to stand for 15 minutes in order to await sedimentation of the particles, and the measurement was then carried out.

The following buffer is used as the aqueous solution: 10 mM Tris, 150 mM NaCl, 0.1% bovine serum albumin (BSA), 0.05% Polysorbate 20 (Tween™ 20), pH 7.4 in distilled water.

The measurement is carried out in a Tecan Safire fluorescence reader at an excitation wavelength of 490 nm and at emission wavelengths of 535 nm for detection of the first fluorescence marker (=Alexa 647-conjugated antibody fragment (Jackson Immuno Research, AffiniPure F(ab')₂ Fragment Goat Anti-Human IgG F(ab') specific 488) and 580 nm for detection of the second fluorescence marker (=R-Phycoerythrin).

The respective calibration functions are determined analogously to Examples A and B. The corresponding calibration curve is shown in FIG. 5d. FIG. 5d further shows that the simultaneous detection of different binding sites on the analyte (here: rituximab (Mabthera™)) is possible with similar calibration curves.

EXAMPLE E

Measurement of an Assay in a Microplate Without an Opaque Layer

The measurement is carried out using the microplate described in Example D with structural elements but without the opaque lacquer layer.

The following buffer is used as the aqueous solution: 10 mM Tris, 150 mM NaCl, 0.1% bovine serum albumin (BSA), 0.05% Polysorbate 20 (Tween™ 20), pH 7.4 in distilled water.

The assay is carried out according to Example A using the following stock solution comprising functionalised particles and fluorescence marker: 600 µl of a pre-diluted suspension of Protein A-Sepharose® 4B Fast Flow beads and 1.06 µl of the fluorescence marker Alexa488 AffiniPure F(ab')₂ Fragment Goat Anti-Human IgG, F(ab')₂ specific (Jackson Immuno Research Art. No. 109-546-097) in 478 µl of buffer. In each case 54 µl thereof are incubated for 30 minutes as described in Example A on a Variomag Monoshake shaker (H+P) with in each case 6 µl of a sample from the calibration series of rituximab (Mabthera™). The microplate is then allowed to stand for 15 minutes to await sedimentation of the particles, and the measurement is then carried out.

An automated fluorescence microscope of type NyONE (SynenTec, Elmshorn, Germany) is used for the measurement. With a 10×objective from Olympus, an image positioned centrally in the middle of the well is recorded in each case and the fluorescence intensity in the image is measured.

A calibration function is determined analogously to Example A. The corresponding calibration curve is shown in FIG. 5e.

The invention claimed is:
1. Method for quantitatively determining biological analytes in an aqueous solution in the presence of one or more functionalised surfaces, comprising
  (a) introducing at least one type of functionalised particle into a measuring chamber which has a detection region which is accessible to light through the bottom of the measuring chamber, and a separation region which is not accessible to light through the bottom of the measuring chamber;
  (b) introducing a sample comprising at least one type of biological analyte into the measuring chamber;
  (c) introducing at least one type of fluorescence marker into the measuring chamber;

(c') mixing the at least one type of functionalised particle, the sample and the at least one type of fluorescence marker in the measuring chamber;

(c") separating the unbound fluorescence markers from the bound fluorescence markers so that the bound fluorescence markers are located in the separation region;

(d) measuring the fluorescence emission of the unbound fluorescence markers in the detection region; and (e) determining the quantity and/or concentration of the biological analyte or analytes using the measured fluorescence emission from (d), wherein the functionalised surfaces comprise the functionalised particles, which are particles of polymer or a polymer mixture, on the surface of which there are catcher molecules which bind to the biological analyte or analytes and/or to the fluorescence marker or markers, and wherein the functionalised particles have a mean diameter in a range of from about 20 to about 200 μm.

2. The method according to claim 1, wherein (a), (b) and (c) are carried out sequentially or at least two of (a)-(c) are carried out simultaneously.

3. The method according to claim 1, wherein (a) and/or (c) are carried out before remaining steps and with a time interval of greater than 12 hours between (a) and/or (c).

4. The method according to claim 1, wherein the method is a direct immunoassay, sandwich immunoassay, displacement immunoassay, competitive immunoassay or secondary immunoassay.

5. The method according to claim 1, wherein the functionalised particles have a mean diameter in a range of from about 80 to about 200 μm.

6. The method according to claim 1, wherein the functionalised particles have a binding capacity of more than 200 mg IgG or analyte per mL.

7. The method according to claim 1, further comprising:
(a') treating at least one surface inside the measuring chamber with a coating buffer that promotes binding of a catcher molecule, and adding at least one type of catcher molecule.

8. The method according to claim 7, wherein in (a'), the at least one type of catcher molecule is added in solution.

9. The method according to claim 1, wherein the at least one type of functionalised particle is not a magnetic particle.

* * * * *